US010093616B2

(12) United States Patent
Roberge et al.

(10) Patent No.: US 10,093,616 B2
(45) Date of Patent: Oct. 9, 2018

(54) PREPARATION OF HYDROXY-BENZYLBENZENE DERIVATIVES

(71) Applicant: THERACOS SUB, LLC, Marlborough, MA (US)

(72) Inventors: Jacques Roberge, Princeton, NJ (US); Carine Vaxelaire, Shanghai (CN); Baohu Liu, Shanghai (CN); Ge Xu, Shanghai (CN); Jian Zhang, Shanghai (CN); Xinxing Tang, Shanghai (CN); Baihua Xu, Malden, MA (US)

(73) Assignee: THERACOS SUB, LLC, Marlborough, MA (US)

( * ) Notice: Subject to any disclaimer, the term of this patent is extended or adjusted under 35 U.S.C. 154(b) by 0 days.

(21) Appl. No.: 15/238,665

(22) Filed: Aug. 16, 2016

(65) Prior Publication Data

US 2016/0355471 A1  Dec. 8, 2016

Related U.S. Application Data

(62) Division of application No. 14/511,725, filed on Oct. 10, 2014, now Pat. No. 9,464,043.

(30) Foreign Application Priority Data

Oct. 12, 2013 (WO) .................. PCT/CN2013/001227

(51) Int. Cl.
| C07C 309/73 | (2006.01) |
| C07C 303/28 | (2006.01) |
| C07C 309/75 | (2006.01) |
| C07C 37/055 | (2006.01) |
| C07C 41/16  | (2006.01) |
| C07C 41/26  | (2006.01) |
| C07C 41/40  | (2006.01) |

(52) U.S. Cl.
CPC .......... *C07C 309/73* (2013.01); *C07C 37/055* (2013.01); *C07C 41/16* (2013.01); *C07C 41/26* (2013.01); *C07C 41/40* (2013.01); *C07C 303/28* (2013.01); *C07C 309/75* (2013.01); *C07B 2200/05* (2013.01); *C07B 2200/13* (2013.01); *C07C 2601/02* (2017.05)

(58) Field of Classification Search
USPC ............................................. 568/22, 23, 25
See application file for complete search history.

(56) References Cited

U.S. PATENT DOCUMENTS

| 5,663,377 | A  | 9/1997  | Curley, Jr. et al. |
| 6,069,238 | A  | 5/2000  | Hitchcock et al. |
| 6,414,126 | B1 | 7/2002  | Ellsworth et al. |
| 6,515,117 | B2 | 2/2003  | Ellsworth et al. |
| 6,555,519 | B2 | 4/2003  | Washburn |
| 6,683,056 | B2 | 1/2004  | Washburn et al. |
| 6,774,112 | B2 | 8/2004  | Gougoutas |
| 6,936,590 | B2 | 8/2005  | Washburn et al. |
| 7,022,725 | B2 | 4/2006  | Momose et al. |
| 7,094,763 | B2 | 8/2006  | Rybczynski et al. |
| 7,371,732 | B2 | 5/2008  | Eickelmann et al. |
| 7,375,090 | B2 | 5/2008  | Himmelsbach et al. |
| 7,375,213 | B2 | 5/2008  | Deshpande et al. |
| 7,393,836 | B2 | 7/2008  | Eckhardt et al. |
| 7,417,032 | B2 | 8/2008  | Eckhardt et al. |
| 7,419,959 | B2 | 9/2008  | Eckhardt et al. |
| 7,838,498 | B2 | 11/2010 | Chen et al. |
| 7,838,499 | B2 * | 11/2010 | Chen ................... C07D 309/10 514/23 |
| 8,106,021 | B2 | 1/2012  | Chen et al. |
| 8,283,454 | B2 | 10/2012 | Liou et al. |
| 9,464,043 | B2 | 10/2016 | Roberge et al. |
| 2002/0111315 | A1 | 8/2002 | Washburn et al. |
| 2003/0064935 | A1 | 4/2003 | Gougoutas |
| 2003/0087843 | A1 | 5/2003 | Washburn |
| 2003/0114390 | A1 | 6/2003 | Washburn et al. |
| 2004/0138148 | A1 | 7/2004 | Fushimi et al. |
| 2004/0138439 | A1 | 7/2004 | Deshpande et al. |
| 2004/0230045 | A1 | 11/2004 | Shen et al. |
| 2004/0259819 | A1 | 12/2004 | Frick et al. |
| 2005/0014704 | A1 | 1/2005 | Frick et al. |
| 2005/0032712 | A1 | 2/2005 | Urbanski |
| 2005/0037980 | A1 | 2/2005 | Rybczynski et al. |
| 2005/0124555 | A1 | 6/2005 | Tomiyama et al. |
| 2005/0187168 | A1 | 8/2005 | Eickelmann et al. |
| 2005/0209166 | A1 | 9/2005 | Eckhardt et al. |
| 2005/0209309 | A1 | 9/2005 | Sato et al. |
| 2005/0233982 | A1 | 10/2005 | Himmelsbach et al. |
| 2005/0233988 | A1 | 10/2005 | Nomura et al. |
| 2006/0009400 | A1 | 1/2006 | Eckhardt et al. |

(Continued)

FOREIGN PATENT DOCUMENTS

| CA | 2 539 032 A1 | 3/2005 |
| CA | 2 548 353 A1 | 7/2005 |

(Continued)

OTHER PUBLICATIONS

Armarego, et al., Purification of Laboratory Chemicals. Published by Elsevier, p. 14-17 and 37. (2003).
Arakawa, et al., "Improved diabetic syndrome in C57BL/KsJ-db/db mice by oral administration of the Na$^+$-glucose cotransporter inhibitor T-1095," *Br J Pharmacol*, vol. 132, pp. 578-586 (2001).
Banker, G.S. et al., "Modern Pharmaceutics, 3ed.", Marcel Dekker, New York, 1996, p. 596.
Caira, et al., "Crystalline Polymorphism of Organize Compounds," *Topics in Current Chemistry*, vol. 198, pp. 163-208 (1998).
Isaji, M., "Sodium-glucose cotransporter inhibitors for diabetes," *Current Opinion in Investigational Drugs*, 2007, vol. 8, No. 4, pp. 285-292.
Ishikawa, et al., "SGLT Gene Expression in Primary Lung Cancers and Their Metastatic Lesions," *Jpn J Cancer Res*, vol. 92, pp. 874-879 (2001).

(Continued)

*Primary Examiner* — Pancham Bakshi
(74) *Attorney, Agent, or Firm* — Mintz, Levin, Cohn, Ferris, Glovsky and Popeo, P.C.

(57) ABSTRACT

Methods for preparing intermediates of SGLT2 inhibitors are provided, including crystalline forms and methods of crystallizing intermediates.

15 Claims, 7 Drawing Sheets

(56) References Cited

U.S. PATENT DOCUMENTS

| | | |
|---|---|---|
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0122126 A1 | 6/2006 | Imamura et al. |
| 2006/0142210 A1 | 6/2006 | Eckhardt et al. |
| 2006/0166899 A1 | 7/2006 | Teranishi et al. |
| 2006/0189548 A1 | 8/2006 | Himmelsbach et al. |
| 2006/0234953 A1 | 10/2006 | Himmelsbach et al. |
| 2006/0234954 A1 | 10/2006 | Urbanski |
| 2006/0235062 A1 | 10/2006 | Neogi et al. |
| 2006/0247179 A1 | 11/2006 | Fushimi et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0072896 A1 | 3/2007 | Khan et al. |
| 2007/0161787 A1 | 7/2007 | Imamura et al. |
| 2007/0185197 A1 | 8/2007 | Fujikura et al. |
| 2007/0197450 A1 | 8/2007 | Fushimi et al. |
| 2007/0249544 A1 | 10/2007 | Himmelsbach et al. |
| 2007/0238866 A1 | 11/2007 | Deshpande et al. |
| 2007/0275907 A1 | 11/2007 | Chen et al. |
| 2008/0004336 A1 | 1/2008 | Gougoutas et al. |
| 2008/0027014 A1 | 1/2008 | Nomura et al. |
| 2008/0132563 A1 | 6/2008 | Kakinuma et al. |
| 2008/0242596 A1 | 10/2008 | Chen et al. |
| 2008/0318874 A1 | 12/2008 | Matsuoka et al. |
| 2009/0023913 A1 | 1/2009 | Eckhardt et al. |
| 2009/0030006 A1 | 1/2009 | Kobayashi et al. |
| 2009/0030198 A1 | 1/2009 | Goodwin et al. |
| 2009/0118201 A1 | 5/2009 | Chen et al. |
| 2009/0156516 A1 | 6/2009 | Chen et al. |
| 2010/0056618 A1 | 3/2010 | Mascitti et al. |
| 2010/0063141 A1 | 3/2010 | Seed et al. |
| 2010/0222599 A1* | 9/2010 | Liou .................. C07D 309/08 548/532 |
| 2013/0267694 A1 | 10/2013 | Xu et al. |
| 2014/0051648 A1 | 2/2014 | Wang |
| 2015/0210634 A1 | 7/2015 | Roberge et al. |

FOREIGN PATENT DOCUMENTS

| | | |
|---|---|---|
| CN | 1407990 A | 4/2003 |
| CN | 101754972 A | 6/2010 |
| CN | 101790311 A | 7/2010 |
| CN | 102149280 A | 8/2011 |
| CN | 102933592 A | 2/2013 |
| EP | 1489089 A1 | 12/2004 |
| EP | 1 783 110 A1 | 5/2007 |
| EP | 1 803 721 A1 | 7/2007 |
| EP | 1 852 439 A1 | 11/2007 |
| EP | 1908757 A1 | 4/2008 |
| EP | 2009010 A1 | 12/2008 |
| WO | 98/31697 A1 | 7/1998 |
| WO | 01/027128 A1 | 4/2001 |
| WO | 01/074834 A1 | 10/2001 |
| WO | 01/074835 A1 | 10/2001 |
| WO | 02/083066 A2 | 10/2002 |
| WO | 02/083066 A3 | 10/2002 |
| WO | 03/020737 A1 | 3/2003 |
| WO | 03/099836 A1 | 12/2003 |
| WO | 2004/063209 A2 | 7/2004 |
| WO | 2004/063209 A3 | 7/2004 |
| WO | 2005/003196 A1 | 1/2005 |
| WO | 2008/034859 A1 | 1/2005 |
| WO | 2005/021566 A2 | 3/2005 |
| WO | 2005/021566 A3 | 3/2005 |
| WO | 2005/063785 A2 | 7/2005 |
| WO | 2005/063785 A3 | 7/2005 |
| WO | 2005/085237 A1 | 9/2005 |
| WO | 2005/092877 A1 | 10/2005 |
| WO | 2006/002912 A1 | 1/2006 |
| WO | 2006/008038 A1 | 1/2006 |
| WO | 2006/010557 A1 | 2/2006 |
| WO | 2006/011469 A1 | 2/2006 |
| WO | 2006/018150 A1 | 2/2006 |
| WO | 2006/034489 A2 | 3/2006 |
| WO | 2006/034489 A3 | 3/2006 |
| WO | 2006/037537 A2 | 4/2006 |
| WO | 2006/037537 A3 | 4/2006 |
| WO | 2006/064033 A2 | 6/2006 |
| WO | 2006/064033 A3 | 6/2006 |
| WO | 2006/073197 A1 | 7/2006 |
| WO | 2006/080421 A1 | 8/2006 |
| WO | 2006/108842 A1 | 10/2006 |
| WO | 2006/110654 A1 | 10/2006 |
| WO | 2006/117359 A1 | 11/2006 |
| WO | 2006/117360 A1 | 11/2006 |
| WO | 2006/120208 A1 | 11/2006 |
| WO | 2007/000445 A1 | 1/2007 |
| WO | 2007/014894 A2 | 2/2007 |
| WO | 2007/014894 A3 | 2/2007 |
| WO | 2007/025943 A2 | 3/2007 |
| WO | 2007/025943 A3 | 3/2007 |
| WO | 2007/028814 A1 | 3/2007 |
| WO | 2007/114475 A1 | 10/2007 |
| WO | 2007/136116 A2 | 11/2007 |
| WO | 2007/136116 A3 | 11/2007 |
| WO | 2008/002824 A1 | 1/2008 |
| WO | 2008/049923 A1 | 5/2008 |
| WO | 2008/069327 A1 | 6/2008 |
| WO | 2008/144346 A2 | 11/2008 |
| WO | 2009/026537 A1 | 2/2009 |
| WO | 2009/035969 A1 | 3/2009 |
| WO | 2010/009243 A1 | 1/2010 |
| WO | 2010/022313 A2 | 2/2010 |
| WO | 2010/147430 A2 | 12/2010 |
| WO | 2012/165914 A2 | 12/2012 |

OTHER PUBLICATIONS

Morissette, et al., "High-throughput crystallization: polymorphs, salts, co-crystals and solvates of pharmaceutical solids," *Advanced Drug Delivery Reviews*, vol. 56, pp. 275-300. (2004).

Oku, et al., "T-1095 an Inhibitor of Renal Na$^+$-Glucose Cotransporters, May Provide a Novel Approach to Treating Diabetes," *Diabetes*, vol. 48, pp. 1794-1800 (1999).

Rodriguez-Spong, et al., "General principles of pharmaceutical solid polymorphism: a supramolecular perspective," *Advanced Drug Delivery Reviews*, vol. 56, pp. 241-274 (2004).

Santer, et al, "Molecular Analysis of the SGLT2 Gene in Patients with Renal Glucosuria", *J Am Soc Nephrol*, vol. 14, pp. 2873-2882 (2003).

Washburn, "Evolution of sodium glucose co-transporter 2 inhibitors as anti-diabetic agents," *Expert Opin Ther Patents*, vol. 19, pp. 1485-1499 (2009).

Wolff, Manfred E., "Burger's Medicinal Chemistry, 5ed, Part I", John Wiley & Sons, 1995, pp. 975-977.

European Search Report dated Aug. 1, 2011, issued in related European Patent Application No. 09808859.

European Search Report for European Application No. EP 11791943. 1, dated Oct. 8, 2013.

International Search Report dated Nov. 17, 2008, for International Application No. PCT/US08/74058, filed Aug. 22, 2008, 2 pages.

International Search Report dated Apr. 26, 2010, for International Application No. PCT/US2009/054585 filed on Aug. 21, 2009, 4 pages.

International Search Report for International Application No. PCT/CN2010/073865, dated Mar. 24, 2011.

International Search Report for International Application No. PCT/CN2011/075554, dated Sep. 29, 2011.

International Search Report from International Application No. PCT/CN2013/001227 dated Jul. 18, 2014.

International Search Report for International Application No. PCT/CN2014/000898 dated Jan. 19, 2015.

(56) References Cited

OTHER PUBLICATIONS

Office Action for Colombian Patent Application No. 12.212.781, dated Jan. 14, 2014.
Xu, B. et al. (Aug. 2011, e-published Jun. 16, 2011). "C-aryl glucosides substituted at the 4'-position as potent and selective renal sodium-dependent glucose co-transporter 2 (SGLT2) inhibitors for the treatment of type 2 diabetes," *Bioorg Med Chem Lett* 21(15):4465-4470.

\* cited by examiner

Figure 4

| Pos. [°2Th.] | Height [cts] | FWHM Left [°2Th.] | d-spacing [Å] | Rel. Int. [%] |
|---|---|---|---|---|
| 11.23 | 303.20 | 0.05 | 7.88 | 2.13 |
| 14.11 | 1095.91 | 0.05 | 6.28 | 7.72 |
| 14.21 | 871.46 | 0.04 | 6.23 | 6.14 |
| 14.33 | 1915.34 | 0.05 | 6.18 | 13.48 |
| 15.49 | 232.10 | 0.04 | 5.72 | 1.63 |
| 15.88 | 473.11 | 0.05 | 5.58 | 3.33 |
| 17.10 | 222.86 | 0.05 | 5.18 | 1.57 |
| 20.69 | 807.14 | 0.04 | 4.29 | 5.68 |
| 21.13 | 1904.53 | 0.05 | 4.21 | 13.41 |
| 21.39 | 1934.28 | 0.06 | 4.15 | 13.62 |
| 21.65 | 14204.15 | 0.09 | 4.10 | 100.00 |
| 21.72 | 6286.56 | 0.03 | 4.10 | 44.26 |
| 22.13 | 4874.85 | 0.06 | 4.01 | 34.32 |
| 22.19 | 4501.01 | 0.05 | 4.01 | 31.69 |
| 23.38 | 268.52 | 0.12 | 3.80 | 1.89 |
| 23.68 | 150.21 | 0.16 | 3.75 | 1.06 |
| 24.10 | 382.86 | 0.09 | 3.69 | 2.70 |
| 24.30 | 1257.98 | 0.09 | 3.66 | 8.86 |
| 24.44 | 1472.66 | 0.06 | 3.64 | 10.37 |
| 24.51 | 1157.45 | 0.05 | 3.64 | 8.15 |
| 26.64 | 148.25 | 0.05 | 3.34 | 1.04 |
| 28.55 | 722.50 | 0.08 | 3.12 | 5.09 |
| 28.76 | 1025.58 | 0.06 | 3.10 | 7.22 |
| 28.84 | 538.64 | 0.05 | 3.10 | 3.79 |
| 31.14 | 719.17 | 0.05 | 2.87 | 5.06 |
| 34.31 | 340.09 | 0.06 | 2.61 | 2.39 |
| 35.66 | 291.53 | 0.05 | 2.52 | 2.05 |
| 37.25 | 235.60 | 0.08 | 2.41 | 1.66 |

| Pos. [°2Th.] | Height [cts] | FWHM Left [°2Th.] | d-spacing [Å] | Rel. Int. [%] |
| --- | --- | --- | --- | --- |
| 14.29 | 2010.21 | 0.06 | 6.20 | 66.32 |
| 14.99 | 238.60 | 0.08 | 5.91 | 7.87 |
| 15.77 | 702.83 | 0.10 | 5.62 | 23.19 |
| 16.00 | 945.12 | 0.04 | 5.54 | 31.18 |
| 17.39 | 225.15 | 0.10 | 5.10 | 7.43 |
| 17.64 | 509.21 | 0.06 | 5.03 | 16.80 |
| 20.92 | 1818.96 | 0.10 | 4.25 | 60.01 |
| 21.05 | 2207.31 | 0.04 | 4.22 | 72.82 |
| 21.68 | 979.74 | 0.08 | 4.10 | 32.32 |
| 21.82 | 1987.77 | 0.05 | 4.07 | 65.58 |
| 21.91 | 3031.15 | 0.04 | 4.06 | 100.00 |
| 23.41 | 295.30 | 0.20 | 3.80 | 9.74 |
| 24.32 | 955.79 | 0.05 | 3.66 | 31.53 |
| 24.58 | 1265.00 | 0.04 | 3.62 | 41.73 |
| 25.38 | 158.56 | 0.20 | 3.51 | 5.23 |
| 26.80 | 333.11 | 0.05 | 3.33 | 10.99 |
| 28.75 | 999.20 | 0.05 | 3.11 | 32.96 |
| 31.39 | 212.95 | 0.15 | 2.85 | 7.03 |
| 34.47 | 163.37 | 0.20 | 2.60 | 5.39 |
| 35.40 | 160.42 | 0.13 | 2.54 | 5.29 |

Figure 8

| Shift cm$^{-1}$ | a.u. | Shift cm$^{-1}$ | a.u. | Shift cm$^{-1}$ | a.u. | Shift cm$^{-1}$ | a.u. |
|---|---|---|---|---|---|---|---|
| 49.4 | 174 | 275.6 | 343 | 1176.7 | 531 | 2959.5 | 327 |
| 60.1 | 267 | 389.8 | 293 | 1179.8 | 308 | 2961.9 | 372 |
| 63.7 | 319 | 393.3 | 299 | 1182.9 | 228 | 2964.3 | 268 |
| 67.3 | 597 | 396.7 | 293 | 1201.4 | 236 | 2966.7 | 256 |
| 70.8 | 936 | 488.9 | 229 | 1204.5 | 452 | 2976.2 | 307 |
| 74.4 | 1421 | 630.1 | 299 | 1207.6 | 799 | 2978.6 | 402 |
| 78.0 | 1389 | 633.4 | 475 | 1210.7 | 810 | 2981.0 | 400 |
| 81.6 | 1258 | 636.8 | 304 | 1213.8 | 494 | 2983.4 | 321 |
| 85.1 | 1165 | 745.9 | 224 | 1216.9 | 257 | 2985.7 | 231 |
| 88.7 | 1503 | 749.2 | 246 | 1339.2 | 256 | 3009.5 | 263 |
| 92.3 | 2003 | 768.8 | 264 | 1342.2 | 294 | 3011.9 | 228 |
| 95.8 | 2528 | 772.1 | 655 | 1444.6 | 218 | 3014.3 | 275 |
| 99.4 | 2955 | 775.4 | 1211 | 1595.5 | 298 | 3016.6 | 317 |
| 103.0 | 2993 | 778.6 | 1554 | 1598.4 | 337 | 3019.0 | 363 |
| 106.5 | 3137 | 781.9 | 1244 | 1601.4 | 235 | 3021.4 | 394 |
| 110.1 | 3246 | 785.2 | 687 | 2872.9 | 221 | 3023.7 | 375 |
| 113.6 | 2912 | 788.4 | 311 | 2875.3 | 254 | 3026.1 | 280 |
| 117.2 | 2260 | 808.0 | 248 | 2877.7 | 217 | 3063.8 | 221 |
| 120.8 | 1524 | 814.5 | 244 | 2918.8 | 226 | 3068.5 | 245 |
| 124.3 | 974 | 817.8 | 267 | 2921.2 | 254 | 3070.9 | 333 |
| 127.9 | 613 | 821.0 | 320 | 2923.6 | 326 | 3073.2 | 306 |
| 131.4 | 387 | 824.3 | 218 | 2926.0 | 313 | 3075.6 | 312 |
| 135.0 | 242 | 1092.5 | 231 | 2928.4 | 312 | 3077.9 | 234 |
| 230.2 | 305 | 1095.6 | 351 | 2930.8 | 371 | | |
| 233.7 | 308 | 1098.7 | 343 | 2933.2 | 349 | | |
| 237.2 | 374 | 1161.1 | 452 | 2935.6 | 292 | | |
| 240.7 | 254 | 1164.2 | 735 | 2938.0 | 306 | | |
| 265.2 | 347 | 1167.3 | 1175 | 2940.4 | 286 | | |
| 268.7 | 475 | 1170.5 | 1365 | 2954.7 | 220 | | |
| 272.1 | 456 | 1173.6 | 960 | 2957.1 | 255 | | |

PREPARATION OF HYDROXY-BENZYLBENZENE DERIVATIVES

CROSS-REFERENCES TO RELATED APPLICATIONS

This application is a continuation of U.S. patent application Ser. No. 14/511,725 filed, Oct. 10, 2014, which application claims foreign priority to International Patent Application No. PCT/CN2013/001227, filed Oct. 12, 2013, each of which is incorporated in its entirety herein for all purposes.

BACKGROUND OF THE INVENTION

The sodium-dependent ("active") glucose cotransporters (SGLTs), including SGLT1 (found predominantly in the intestinal brush border) and SGLT2 (localized in the renal proximal tubule), have been significantly evaluated. In particular, SGLT2 has been found to be responsible for the majority of glucose reuptake by the kidneys. Inhibition of renal SGLT is now considered a useful approach to treating hyperglycemia by increasing the amount of glucose excreted in the urine (Arakawa K, et al., *Br J Pharmacol* 132:578-86, 2001; Oku A, et al., *Diabetes* 48:1794-1800, 1999). The potential of this therapeutic approach is further supported by recent findings that mutations in the SGLT2 gene occur in cases of familial renal glucosuria, an apparently benign syndrome characterized by urinary glucose excretion in the presence of normal serum glucose levels and the absence of general renal dysfunction or other disease (Santer R, et al., *J Am Soc Nephrol* 14:2873-82, 2003). Therefore, compounds which inhibit SGLT, particularly SGLT2, are promising candidates for use as antidiabetic drugs (reviewed in Washburn W N, *Expert Opin Ther Patents* 19:1485-99, 2009). In addition, since cancer cells show increased glucose uptake in comparison to their normal counterparts, SGLT inhibition has been proposed as a method for treating cancer by starving cancer cells. For example, studies suggest that SGLT2 plays a role in glucose uptake in metastatic lesions of lung cancer (Ishikawa N, et al., *Jpn J Cancer Res* 92:874-9, 2001). Thus, SGLT2 inhibitors may also be useful as anticancer agents.

In addition to pharmaceutical activity, a further consideration for the successful development of a medicament is the parameters which are connected with the physical nature of the active substance itself. Some of these parameters are stability of the active substance under various environmental conditions, stability of the active substance during production of the pharmaceutical formulation and the stability of the active substance in the final medicament compositions. In order to provide the necessary stability, the pharmaceutically active substance used in the medicament should be as pure as possible, leading to its stability in long-term storage under various environmental conditions.

The compounds prepared according to the present invention have been prepared previously according to the methods described in WO2001/027128, US2004/0230045, US2005/0124555, US2006/0122126, US2007/0238866, US2007/0275907, US2008/0242596, US2008/0132563, US2008/0318874, WO2008/034859, US2009/0030006, US2009/0030198, US2009/0118201, US2009/0156516, US2010/0056618, US2010/0063141 and WO2010/147430. Other compounds prepared by the methods of the present invention that have been prepared previously by different methods can be found in WO2005/003196.

BRIEF SUMMARY OF THE INVENTION

In some embodiments, the present invention provides a method for preparing the compound Formula I:

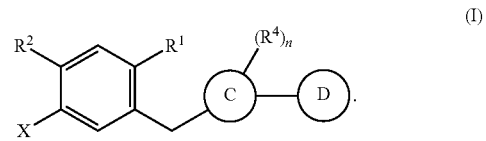

The method includes forming a reaction mixture including a compound of Formula II:

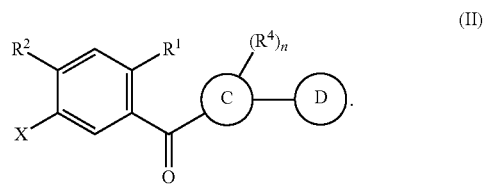

The reaction mixture also includes a silane reducing agent, a catalyst, and a solvent. The reaction mixture is under conditions suitable to prepare the compound of Formula I.

Radical X can be bromo or iodo. Radical $R^1$ can be hydrogen, halogen, $C_1$-$C_3$ alkyl, $C_2$-$C_4$ alkene, $C_2$-$C_4$ alkyne, $C_3$-$C_6$ cycloalkyl, or —CN. Each $R^2$ and $R^3$ can independently be hydrogen, halo, hydroxy, $C_1$-$C_3$ alkyl, $C_2$-$C_4$ alkenyl, $C_1$-$C_3$ alkoxy, $C_1$-$C_3$ alkyl-hydroxy, $C_3$-$C_6$ cycloalkyl, ($C_1$-$C_3$ alkoxy)$C_1$-$C_3$ alkyl, ($C_1$-$C_3$ haloalkoxy) $C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy) $C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy, ($C_3$-$C_6$ cycloalkyl)$C_2$-$C_4$ alkynyloxy, —C(O)H, —C(O)OH, or —C(O)O—$C_1$-$C_3$ alkyl. At least one $R^3$ can be $C_1$-$C_3$ alkoxy, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

Each $R^4$ of Formula I can independently be hydrogen, halo, —$OR^{4a}$, $C_1$-$C_3$ alkyl, $C_2$-$C_4$ alkenyl, $C_1$-$C_3$ alkoxy, $C_1$-$C_3$ alkyl-hydroxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy) $C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy, ($C_3$-$C_6$ cycloalkyl)$C_2$-$C_4$ alkynyloxy, —C(O)H, —C(O)OH, or —C(O)O—$C_1$-$C_3$ alkyl, wherein $R^{4a}$ can be hydrogen or a silyl group. At least one $R^4$ of Formula I can be —$OR^{4a}$.

Ring C can be an aryl or a heteroaryl. And ring D can be absent or an aryl or a heteroaryl. Subscript n can be an integer from 1 to 4. The alkyl, alkoxy, cycloalkyl, alkenyloxy, alkynyloxy, cycloalkoxy, hydroxyalkoxy, or heterocycloalkoxy groups or portions thereof of Formulas I and II and the radicals above can optionally be partially or completely fluorinated. One or more hydrogen atoms of Formulas I and II and the radicals above can optionally be replaced with deuterium.

In some embodiments, the present invention provides a crystalline form of the compound having the structure:

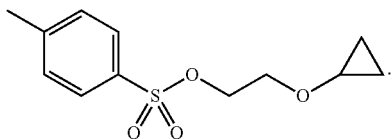

In some embodiments, the present invention provides a crystalline form of a compound of the present invention which is isotopically labeled.

In some embodiments, the present invention provides a method of preparing a compound of Formula III:

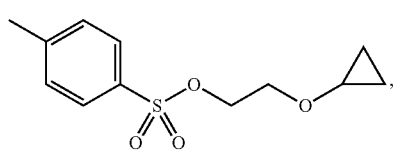 [SMILES: Cc1ccc(S(=O)(=O)OCCOC2CC2)cc1]

(III)

wherein the method includes a step (a) of forming a first reaction mixture including Mg and a compound having the structure:

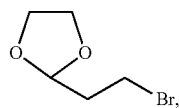

in tetrahydrofuran solvent, under conditions suitable to form an intermediate compound having the structure:

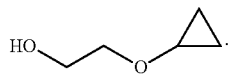

The method also includes a step (b) of contacting the first reaction mixture with water and 2-methyl-tetrahydrofuran such that the intermediate of step (a) is substantially dissolved in the 2-methyl-tetrahydrofuran. The method also includes a step (c) of forming a second reaction mixture with 4-methylbenzene-1-sulfonyl chloride (Tosyl-Cl) and the 2-methyl-tetrahydrofuran of step (b) containing the intermediate of step (a), under conditions suitable to form the compound of Formula III.

In some embodiments, the present invention provides a method for preparing a crystalline form of a compound having the structure:

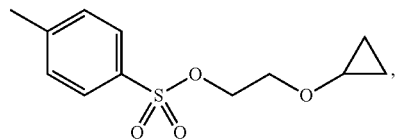 [SMILES: Cc1ccc(S(=O)(=O)OCCOC2CC2)cc1]

wherein the method includes a step (a) of mixing 2-cyclopropoxyethyl-4-methylbenzenesulfonate and a first solvent that is a polar protic solvent to form a solution, and a step (b) of adding a second solvent to the solution to provide a mixture, under conditions suitable to form the crystalline form of the compound.

BRIEF DESCRIPTION OF THE DRAWINGS

FIG. 4 provides a Table of XRPD data for the XRPD spectra in FIG. 2 and FIG. 3.

FIG. 8 provides a Raman peak list for the Raman spectra in FIG. 7.

DETAILED DESCRIPTION OF THE INVENTION

I. General

Figure 1:
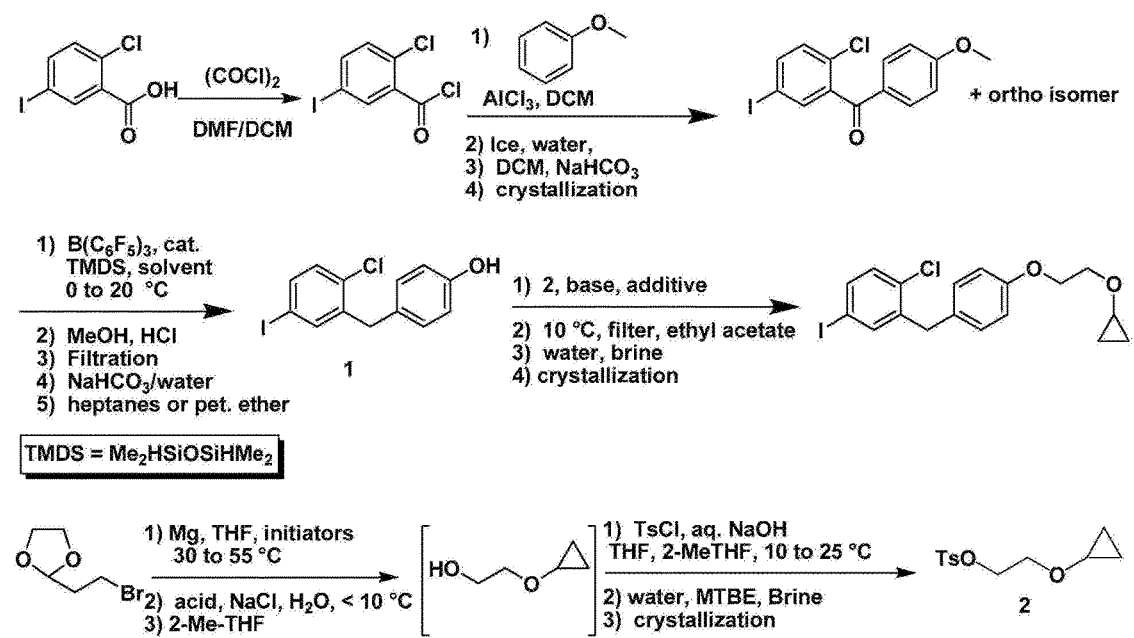
FIG. 1 provides a scheme for the preparation of 2-(4-(2-cyclopropoxyethoxy)benzyl)-1-chloro-4-iodobenzene.

The present invention provides methods of preparing intermediate compounds for the preparation of sodium-dependent glucose cotransporter SGLT inhibitors. Some compounds can be prepared in high yield and purity by performing a simultaneous reduction of a benzophenone ketone and dealkylation of a methoxyphenyl group using a boron catalyst and tetramethyldisiloxane in toluene. Other intermediate compounds can be prepared using a Barbier-like magnesium mediated intramolecular ring opening/cyclization where the product is isolated using 2-methyl-tetrahydrofuran, which is used as the solvent in the following step without concentration, affording the product in high purity and yield. Finally, the present invention also provides a crystalline compound, and methods for preparing the crystalline compound.

II. Definitions

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Silane reducing agent" refers to an agent used in the reduction of a ketone and/or a dealkylation step that contains a silane functional group, "$R_3Si$—H". Representative silane reducing agents include, but are not limited to, tetramethyldisiloxane (TMDS), pentamethyldisiloxane (PMDS), polymethylhydrosiloxane (PMHS), and $Et_3SiH$. Other silane reducing agents are useful in the methods of the present invention.

"Catalyst" refers to an agent that increases the rate of a chemical reaction, but is not itself consumed in the reaction. The catalysts of the present invention are capable of catalyzing the reduction of a ketone, and of reducing an —OR group to —OH. Catalysts useful in the present invention include Lewis acid catalysts having aluminum, boron, silicon, tin, titanium, zirconium, iron, copper, or zinc, among others. Representative catalysts include, but are not limited to, $B(C_6F_5)_3$, $BF_3$-$Et_2O$, $BF_3$-THF, $BF_3$—$Bu_2O$, $BF_3$-MeCN, $BF_3AcOH$, $BF_3H_3PO_4$, $BF_3$, $AlCl_3$, and trimethylsilyl trifluoromethanesulfonate (TMSOTf). Other catalysts can be useful in the methods of the present invention.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, tetrahydrofuran, diethyl ether, acetone, ethyl acetate, dimethylformamide, acetonitrile and dimethyl sulfoxide. Representative non-polar solvents include alkanes (pentanes, hexanes, etc.), cycloalkanes (cyclopentane, cyclohexane, etc.), benzene, toluene, and 1,4-dioxane. Other solvents are useful in the present invention.

"Alkyl" alone or in combination refers to a monovalent saturated aliphatic hydrocarbon radical having the indicated number of carbon atoms. The radical may be a linear or branched chain and, where specified, optionally substituted with one to three suitable substituents as defined below. Illustrative examples of alkyl groups include, but are not limited to, methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, n-dodecyl, n-tetradecyl, n-hexadecyl, n-octadecyl, n-eicosyl and the like. Preferred alkyl groups include methyl, ethyl, n-propyl and isopropyl. Preferred optional suitable substituents include halo, methoxy, ethoxy, cyano, nitro and amino.

"Alkoxy" and "alkyloxy" alone or in combination refer to an aliphatic radical of the form alkyl-O—, wherein alkyl is as defined above. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

"Alkenyl" alone or in combination refers to a monovalent aliphatic hydrocarbon radical having the indicated number of carbon atoms and at least one carbon-carbon double bond. The radical may be a linear or branched chain, in the E or Z form, and where specified, optionally substituted with one to three suitable substituents as defined below. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional suitable substituents include halo, methoxy, ethoxy, cyano, nitro and amino.

"Alkenyloxy" alone or in combination refer to an aliphatic radical of the form alkenyl-O—, wherein alkenyl is as defined above. Illustrative examples of alkenyloxy groups include, but are not limited to, vinyloxy, 1-propenyloxy, 2-propenyloxy, isopropenyloxy, 1-butenyloxy, 2-butenyloxy, 3-butenyloxy, 1-isobutenyloxy, 2-isobutenyloxy, 1-pentenyloxy, 2-pentenyloxy, 3-pentenyloxy, 4-pentenyloxy, and the like.

"Alkynyl" alone or in combination refers to a monovalent aliphatic hydrocarbon radical having the indicated number of carbon atoms and at least one carbon-carbon triple bond. The radical may be a linear or branched chain and, where specified, optionally substituted with one to three suitable substituents as defined below. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional suitable substituents include halo, methoxy, ethoxy, cyano, nitro and amino.

"Alkynyloxy" alone or in combination refer to an aliphatic radical of the form alkynyl-O—, wherein alkynyl is as defined above. Illustrative examples of alkynyloxy groups include, but are not limited to, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1-hexynyloxy, 2-hexynyloxy, 3-hexynyloxy and the like.

"Halo" or "halogen" means a monovalent halogen radical or atom selected from fluoro, chloro, bromo and iodo. Preferred halo groups are fluoro, chloro and bromo.

"Haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

"Haloalkoxy" refers to an alkoxy radical as described above substituted with one or more halogens. Illustrative examples of haloalkoxy groups include, but are not limited to, trifluoromethoxy, difluoromethoxy and the like.

"Hydroxy" refers to the group "—OH".

"Alkylhydroxy" refers to an alkyl group, as defined above, where at least one of the hydrogen atoms is replaced with a hydroxy group. As for the alkyl group, alkylhydroxy groups can have any suitable number of carbon atoms, such as $C_{1-6}$. Exemplary alkylhydroxy groups include, but are not limited to, hydroxy-methyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Hydroxyalkoxy" and "hydroxyalkyloxy" alone or in combination refer to an aliphatic radical of the form HOalkoxy-, wherein alkoxy is as defined above. Illustrative examples of hydroxyalkoxy groups include, but are not limited to, hydroxymethoxy, hydroxyethoxy, hydroxyethoxy, hydroxypropoxy, hydroxyisopropoxy, hydroxybutoxy, hydroxyisobutoxy, hydroxy-tert-butoxy, hydroxypentoxy, hydroxyisopentoxy, hydroxyhexoxy, hydroxyisohexoxy, hydroxyheptoxy, hydroxyoctoxy and the like.

"Cycloalkyl" alone or in combination refers to a monovalent alicyclic saturated hydrocarbon radical having three or more carbons forming a carbocyclic ring and, where specified, optionally substituted with one to three suitable substituents as defined below. Illustrative examples of cycloalkyl groups include, but are not limited to, cyclopropyl, cyclobutyl, cyclopentyl, cyclohexyl, cycloheptyl, cyclooctyl, cyclononyl and the like. Preferred optional suitable substituents include halo, methyl, ethyl, methoxy, ethoxy, cyano, nitro and amino.

"Cycloalkoxy" alone or in combination refer to an aliphatic radical of the form cycloalkyl-O—, wherein cycloalkyl is as defined above. Illustrative examples of cycloalkoxy groups include, but are not limited to, cyclopropoxy, cyclobutoxy and cyclopentoxy.

"Heterocycloalkyl" alone or in combination refers to a cycloalkyl group as defined above in which one or more carbons in the ring is replaced by a heteroatom selected from N, S and O. Illustrative examples of heterocycloalkyl groups include, but are not limited to, pyrrolidinyl, tetrahydrofuranyl, piperazinyl, tetrahydropyranyl, and the like.

"Heterocycloalkoxy" alone or in combination refer to an aliphatic radical of the form heterocycloalkyl-O—, wherein heterocycloalkyl is as defined above. Illustrative examples of heterocycloalkoxy groups include, but are not limited to, tetrahydrofuranoxy, pyrrolidinoxy and tetrahydrothiophenoxy.

"Aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted with substituents as defined below; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

"Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

"Silyl group" refers to a silyl group of the formula —Si(R)$_3$, wherein each R can be any suitable group such as, but not limited to, hydrogen, alkyl, alkenyl, alkynyl, aryl, and —OSi(R')$_3$, wherein each R' can be any suitable group such as, but not limited to, hydrogen, alkyl, alkenyl, alkynyl, aryl or polysiloxane. Representative silyl groups include, but are not limited to, dimethylsilane, diethylsilane, trimethylsilyl, triethylsilyl, tertbutyldimethylsilyl, tetramethyldisiloxyl (—Si(Me)$_2$OSi(Me)$_2$H), pentamethyldisiloxyl (—Si(Me)$_2$OSi(Me)$_3$), and polymethylhydrosiloxyl (-(Me)(H)Si—O—)$_x$—).

"Acid" refers to a compound that is capable of donating a proton (H$^+$) under the Bronsted-Lowry definition, or is an electron pair acceptor under the Lewis definition. Acids useful in the present invention are Bronsted-Lowry acids that include, but are not limited to, alkanoic acids or carboxylic acids (formic acid, acetic acid, citric acid, lactic acid, oxalic acid, etc.), sulfonic acids and mineral acids, as defined herein. Mineral acids are inorganic acids such as hydrogen halides (hydrofluoric acid, hydrochloric acid, hydrobromice acid, etc.), halogen oxoacids (hypochlorous acid, perchloric acid, etc.), as well as sulfuric acid, nitric acid, phosphoric acid, chromic acid and boric acid. Sulfonic acids include methanesulfonic acid, benzenesulfonic acid, p-toluenesulfonic acid, trifluoromethanesulfonic acid, among others.

"Suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents may be selected from the group consisting of halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxy, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

"Fluorinated" refers to a radical as described above where at least one hydrogen is replaced with a fluorine. When all the available hydrogens are replaced with fluorine, the group can be referred to as "perfluorinated" or "perfluoro", such as "perfluoroalkyl", "perfluoromethyl" or "perfluorophenyl".

"Substantially dissolved" refers to a compound, product or solute dissolved in a solvent, where the majority of the solute is dissolved in the solvent. For example, at least about 75%, 80, 85, 90, 95, or 99% of the solute can be dissolved in the solvent.

III. Methods for Simultaneous Reduction

The present invention provides a method of preparing compounds by simultaneously reducing a ketone and dealkylating an —OR group to form —OH. In some embodiments, the present invention provides a method for preparing the compound Formula I:

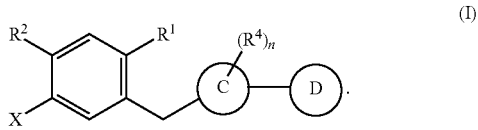

The method includes forming a reaction mixture including a compound of Formula II:

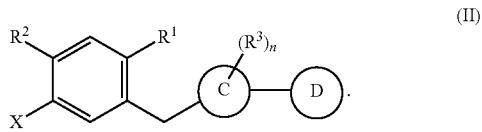

The reaction mixture also includes a silane reducing agent, a catalyst, and a solvent. The reaction mixture is under conditions suitable to prepare the compound of Formula I.

Radical X can be bromo or iodo. Radical $R^1$ can be hydrogen, halogen, $C_1$-$C_3$ alkyl, $C_2$-$C_4$ alkene, $C_2$-$C_4$ alkyne, $C_3$-$C_6$ cycloalkyl, or —CN. Each $R^2$ and $R^3$ can independently be hydrogen, halo, hydroxy, $C_1$-$C_3$ alkyl, $C_2$-$C_4$ alkenyl, $C_1$-$C_3$ alkoxy, $C_1$-$C_3$ alkyl-hydroxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy) $C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy, ($C_3$-$C_6$ cycloalkyl)$C_2$-$C_4$ alkynyloxy, —C(O)H, —C(O)OH, or —C(O)O—$C_1$-$C_3$ alkyl. At least one $R^3$ can be $C_1$-$C_3$ alkoxy, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

Each $R^4$ of Formula I can independently be hydrogen, halo, —$OR^{4a}$, $C_1$-$C_3$ alkyl, $C_2$-$C_4$ alkenyl, $C_1$-$C_3$ alkoxy, $C_1$-$C_3$ alkyl-hydroxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy) $C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy, ($C_3$-$C_6$ cycloalkyl)$C_2$-$C_4$ alkynyloxy, —C(O)H, —C(O)OH, or —C(O)O—$C_1$-$C_3$ alkyl, wherein $R^{4a}$ can be hydrogen or a silyl group. At least one $R^4$ of Formula I can be —$OR^{4a}$.

Ring C can be an aryl or a heteroaryl. And ring D can be absent or an aryl or a heteroaryl. Subscript n can be an integer from 1 to 4. The alkyl, alkoxy, cycloalkyl, alkenyloxy, alkynyloxy, cycloalkoxy, hydroxyalkoxy, or heterocycloalkoxy groups or portions thereof of Formulas I and II and the radicals above can optionally be partially or completely fluorinated. One or more hydrogen atoms of Formulas I and II and the radicals above can optionally be replaced with deuterium.

In some embodiments, the compound of Formula I can have the structure of Formula Ia:

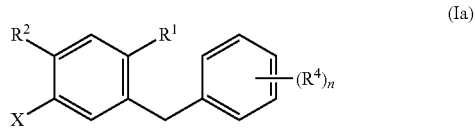

and the compound of Formula II can have the structure of Formula IIa:

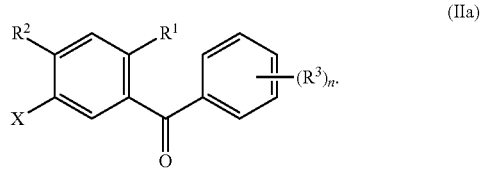

In some embodiments, the compound of Formula Ia can have the structure:

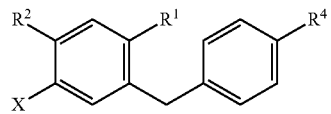

and the compound of Formula IIa can have the structure:

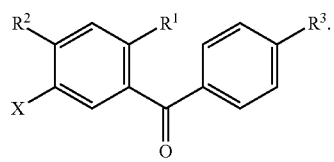

Radical X of Formula I can be bromo or iodo. In some embodiments, X can be iodo.

$R^1$ of Formula I can be any suitable group. In some embodiments, $R^1$ can be hydrogen, halogen, $C_1$-$C_3$ alkyl, $C_2$-$C_4$ alkene, $C_2$-$C_4$ alkyne, $C_3$-$C_6$ cycloalkyl, or —CN. $R^1$ can also be halogen or $C_1$-$C_3$ alkyl. In some embodiments, $R^1$ can be halogen. When $R^1$ is halogen, $R^1$ can be fluoro, chloro, bromo or iodo. In some embodiments, $R^1$ can be chloro.

Radical $R^2$ can be hydrogen, halo, hydroxy, $C_1$-$C_3$ alkyl, $C_2$-$C_4$ alkenyl, $C_1$-$C_3$ alkoxy, $C_1$-$C_3$ alkyl-hydroxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy, ($C_3$-$C_6$ cycloalkyl)$C_2$-$C_4$ alkynyloxy, —C(O)H, —C(O)OH, or —C(O)O—$C_1$-$C_3$ alkyl. In some embodiments, $R^2$ can be hydrogen or $C_1$-$C_3$ alkyl. In some embodiments, $R^2$ can be hydrogen.

Each $R^3$ can independently be hydrogen, halo, hydroxy, $C_1$-$C_3$ alkyl, $C_2$-$C_4$ alkenyl, $C_1$-$C_3$ alkoxy, $C_1$-$C_3$ alkyl-hydroxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy, ($C_3$-$C_6$ cycloalkyl)$C_2$-$C_4$ alkynyloxy, —C(O)H, —C(O)OH, or —C(O)O—$C_1$-$C_3$ alkyl. In some embodiments, each $R^3$ can independently be $C_1$-$C_3$ alkoxy, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy. In some embodiments, each $R^3$ can independently be $C_1$-$C_3$ alkoxy or $C_3$-$C_6$ cycloalkoxy. In some embodiments, each $R^3$ can independently be $C_1$-$C_3$ alkoxy. In some embodiments, each $R^3$ can independently be methoxy, ethoxy, propoxy, or isopropoxy. In some embodiments, $R^3$ can be methoxy.

Each $R^4$ can independently be hydrogen, halo, —$OR^{4a}$, $C_1$-$C_3$ alkyl, $C_2$-$C_4$ alkenyl, $C_1$-$C_3$ alkoxy, $C_1$-$C_3$ alkyl-hydroxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy, ($C_3$-$C_6$ cycloalkyl)$C_2$-$C_4$ alkynyloxy, —C(O)H, —C(O)OH, or —C(O)O—$C_1$-$C_3$ alkyl, wherein $R^{4a}$ can be hydrogen or a silyl group. In some embodiments, at least one $R^4$ can be —$OR^{4a}$. In some embodiments $R^4$ can be —OH. In some embodiments, $R^4$ can be —O-silyl group.

In some embodiments, $R^1$ can be chloro, $R^2$ can be H, $R^3$ can be $C_1$-$C_3$ alkoxy, and $R^4$ can be —$OR^{4a}$. In some embodiments, $R^1$ can be chloro, $R^2$ can be H, $R^3$ can be methoxy, and $R^4$ can be —$OR^{4a}$. In some embodiments, $R^4$ can be —OH.

In some embodiments, subscript n can be an integer from 1 to 4. In some embodiments, subscript n can be 1.

Ring C can be any suitable aryl or heteroaryl ring. Aryl rings useful for ring C include, but are not limited to, phenyl, naphthyl and biphenyl. Heteroaryl rings useful for ring C include, but are not limited to, pyrrole, pyridine, pyran, thiophene, thiopyran, thiazole, imidazole, thiadiazole, pyrazine, pyrimidine, pyridazine, indole and benzothiophene. In some embodiments, ring C can be phenyl, thiadiazole or benzothiophene. In other embodiments, ring C can be phenyl. In some other embodiments, ring C can be thiadiazole.

Ring D can be absent or any suitable heteroaryl ring. Heteroaryl rings useful for ring D include, but are not limited to, pyrrole, pyridine, pyran, thiophene, thiopyran, thiazole, imidazole, thiadiazole, pyrazine, pyrimidine, pyridazine, indole and benzothiophene. In some embodiments, ring D can be absent. In other embodiments, ring D can be furan, thiophene or pyrazine.

In some embodiments, ring C can be phenyl and ring D can be absent. In other embodiments, ring C can be benzothiophene and ring D can be absent. In some other embodiments, ring C can be thiadiazole and ring D can be furan, thiophene or pyrazine.

In some embodiments, $R^1$ can be chloro, $R^2$ can be H, $R^3$ can be methoxy, $R^4$ can be hydroxy, subscript n can be 1, ring C can be phenyl and ring D can be absent.

Any suitable silane reducing agent can be used in the method of the present invention. Representative silane reducing agents include, but are not limited to, tetramethyldisiloxane (TMDS), pentamethyldisiloxane (PMDS), polymethylhydrosiloxane (PMHS), $Et_3SiH$, $Ph_2MeSiH$, $Ph_2SiH_2$, among others. Other silane reducing agents can be found in the Gelest catalog "Silicon, Germanium & Tin Compounds, Metal Alkoxides and Metal Diketonates" and the supplement "Silicon-Based Reducing Agents". In some embodiments, the silane reducing agent can be tetramethyldisiloxane (TMDS), pentamethyldisiloxane (PMDS), polymethylhydrosiloxane (PMHS), or $Et_3SiH$. In some embodiments, the silane reducing agent can be tetramethyldisiloxane (TMDS), pentamethyldisiloxane (PMDS), or $Et_3SiH$. In some embodiments, the silane reducing agent can be tetramethyldisiloxane (TMDS), or pentamethyldisiloxane (PMDS). In some embodiments, the silane reducing agent can be tetramethyldisiloxane (TMDS).

The silane reducing agent can be present in any suitable amount. For example, the silane reducing agent can be present in an amount of at least 1.0 eq. (mol/mol) to the compound of Formula II, such as about 1.0, 2, 3, 4, 5, 6, 7, 8, 9, or about 10.0 eq. (mol/mol). The silane reducing agent can also be present in an amount of from about 1.0 to about 10.0 eq. (mol/mol) to the compound of Formula II, such as of from about 1.0 to about 5.0 eq. (mol/mol), or of from about 1.0 to about 2.0 eq. (mol/mol). In some embodiments, the silane reducing agent can be present in an amount of from about 1.0 to about 5.0 eq. (mol/mol) to the compound of Formula II. In some embodiments, the silane reducing agent can be present in an amount of from about 1.0 to about 2.0 eq. (mol/mol) to the compound of Formula II.

Any suitable catalyst can be used in the method of the present invention. Representative catalysts include Lewis acid catalysts, $B(C_6F_5)_3$, $BF_3$-$Et_2O$, $BF_3$-THF, $BF_3$—$Bu_2O$, $BF_3$-MeCN, $BF_3AcOH$, $BF_3H_3PO_4$, $BF_3$, $AlCl_3$, TMSOTf, and others. In some embodiments, the catalyst can be $B(C_6F_5)_3$, $BF_3$-THF, $BF_3$—$Bu_2O$, $BF_3$-MeCN, $BF_3AcOH$, $BF_3H_3PO_4$, $BF_3$, or TMSOTf. In some embodiments, the catalyst can be $B(C_6F_5)_3$, —$BF_3$-THF, $BF_3$—$Bu_2O$, $BF_3$-MeCN, $BF_3AcOH$, $BF_3H_3PO_4$, or $BF_3$. In some embodiments, the catalyst can be $B(C_6F_5)_3$ or TMSOTf. In some embodiments, the catalyst can be $B(C_6F_5)_3$. Other catalysts useful in the present invention are known in the art and include those having at least one perfluorinated phenyl, such as $B(C_6F_5)(R)_2$, wherein each R can be any suitable substituent, as described above. In some embodiments, the catalyst can be a mixture of $B(C_6F_5)_3$, $BF_3$-$Et_2O$, $BF_3$-THF, $BF_3$—$Bu_2O$, $BF_3$-MeCN, $BF_3AcOH$, $BF_3H_3PO_4$, $BF_3$, $AlCl_3$, or TMSOTf.

The catalyst of the present invention can be present in any suitable amount. For example, the catalyst can be present in an amount of less than 1.0 eq. (mol/mol) to the compound of Formula II, or less than about 0.5, 0.4, 0.3, 0.2 or less than about 0.1 eq. (mol/mol). The catalyst can also be present in an amount of from about 0.0001 to about 0.1 eq. (mol/mol) to the compound of Formula II. In some embodiments, the catalyst can be present in an amount of less than about 0.1 eq. (mol/mol) to the compound of Formula II. The catalyst can also be present in an amount of from about 0.0001 to about 0.1 eq. (mol/mol) to the compound of Formula II. In some embodiments, the catalyst can be present in an amount of less than about 0.01 eq. (mol/mol) to the compound of Formula II. The catalyst can also be present in an amount of from about 0.0001 to about 0.01 eq. (mol/mol) to the compound of Formula II.

The reagents used in the methods of the present invention can be combined in any suitable order. For example, the silane reducing agent and the catalyst can be combined in a first solution which can then be added to a second solution of the compound of Formula II. In some embodiments, the method of forming the compound of Formula I includes forming a first solution of the silane reducing agent and the catalyst, and adding the first solution to a second solution of the compound of Formula II, thus forming the reaction mixture for preparing the compound of Formula I. Alternatively, the second solution of the compound of Formula II can be added to the first solution of the silane reducing agent and the catalyst. In some embodiments, the method of forming the compound of Formula I includes forming a first solution of the silane reducing agent and the catalyst, and adding a second solution of the compound of Formula II to the first solution, thus forming the reaction mixture for preparing the compound of Formula I.

In some embodiments, one or more of the reagents can be divided into two or more portions for addition to the reaction mixture. For example, the silane reducing agent can be divided into two portions where the first portion of the silane reducing agent can be combined with the compound Formula II to form a first solution, and the second portion of the silane reducing agent can be combined with the catalyst to form a second solution. The first solution having the first portion of the silane reducing agent and the compound Formula II can then be added to the second solution having the second portion of the silane reducing agent and the catalyst. The first and second portions of the silane reducing agent can be substantially equal or not equal. For example, the ratio of first portion to the second portion of the silane reducing agent can be from about 1:20 to about 20:1, or about 1:10, 1:9, 1:8, 1:7, 1:6, 1:5, 1:4, 1:3, 1:2, 1:1, 2:1, 3:1, 4:1, 5:1, 6:1, 7:1, 8:1, 9:1 or about 10:1. In some embodiments, the method of forming the compound of Formula I includes forming a first solution of a compound of Formula II and a first portion of a silane reducing agent, forming a second solution of a catalyst and a second portion of the silane reducing agent, and adding the first solution to the second solution, thus forming the reaction mixture for preparing the compound of Formula I. In some embodiments, the ratio of the first and second portions of the silane reducing agent can be about 1:1.

Any suitable solvent can be used in the method of the present invention. Representative solvents include, but are not limited to, pentane, pentanes, hexane, hexanes, heptane, heptanes, petroleum ether, cyclopentanes, cyclohexanes, benzene, toluene, xylene, trifluoromethylbenzene, halobenzenes such as chlorobenzene, fluorobenzene, dichlorobenzene and difluorobenzene, methylene chloride, chloroform, or combinations thereof. The solvents can include those where the compounds of Formula I and II can be poorly soluble or insoluble in the solvent, forming a suspension or a heterogeneous reaction mixture. In some embodiments, the solvent can be pentanes, hexanes, heptanes, cyclopentanes, cyclohexanes, benzene, toluene, xylene, trifluoromethylbenzene, chlorobenzene, or combinations thereof. In some embodiments, the solvent can be pentanes, hexanes, heptanes, cyclopentanes, cyclohexanes, or combinations thereof. In some embodiments, the solvent can be pentanes, hexanes, heptanes, or combinations thereof. In some embodiments, the solvent can be heptanes. In some embodiments, the solvent can be toluene. In some embodiments, the reaction mixture can be a heterogeneous reaction mixture. In some embodiments, the reaction mixture can be a suspension.

The reaction mixture of the method can be at any suitable temperature. For example, the temperature of the reaction mixture can be of from about $-78°$ C. to about $100°$ C., or of from about $-50°$ C. to about $100°$ C., or of from about $-25°$ C. to about $50°$ C., or of from about $-10°$ C. to about $25°$ C., or of from about $0°$ C. to about $20°$ C. In some embodiments, the temperature of the reaction mixture can be of from about $-25°$ C. to about $50°$ C. In some embodiments, the temperature of the reaction mixture can be of from about $-10°$ C. to about $25°$ C. In some embodiments, the temperature of the reaction mixture can be of from about $0°$ C. to about $20°$ C.

The reaction mixture of the method can be at any suitable pressure. For example, the reaction mixture can be at atmospheric pressure. The reaction mixture can be also be exposed to any suitable environment, such as atmospheric gasses, or inert gasses such as nitrogen or argon.

The method of the present invention can provide the compound of Formula I in any suitable yield. For example, the compound of Formula I can be prepared in a yield of at least about 50%, 55, 60, 65, 70, 75, 80, 85, 90 or at least about 95%. In some embodiments, the compound of Formula I can be prepared in at least 75% yield. In some embodiments, the compound of Formula I can be prepared in at least 90% yield. In some embodiments, the compound of Formula I can be prepared in at least 95% yield.

The method of the present invention can provide the compound of Formula I in any suitable purity. For example, the compound of Formula I can be prepared in a purity of at least about 90, 95, 96, 97, 98 or at least about 99%. In some embodiments, the compound of Formula I can be prepared in at least 95% purity. In some embodiments, the compound of Formula I can be prepared in at least 98% purity. In some embodiments, the compound of Formula I can be prepared in at least 99% purity.

$R^{4a}$ can be any suitable silyl group. Silyl groups suitable in the present invention can have the formula —$Si(R)_3$, wherein each R can be any suitable group such as, but not limited to, hydrogen, alkyl, alkenyl, alkynyl, aryl, and —$OSi(R')_3$, wherein each R' can be any suitable group such as, but not limited to, hydrogen, alkyl, alkenyl, alkynyl, aryl or polyhydrosiloxane. In some embodiments, all the R groups are alkyl. In some embodiments, at least one R group can be —$OSi(R')_3$. When at least one R group can be —$OSi(R')_3$, each R' group can be hydrogen, alkyl or polyhydrosiloxane. In some embodiments, $R^{4a}$ can be dimethylsilane, diethylsilane, trimethylsilyl, triethylsilyl, tertbutyldimethylsilyl, tetramethyldisiloxyl (—Si(Me)₂OSi(Me)₂H), pentamethyldisiloxyl (—Si(Me)₂OSi(Me)₃), or polymethylhydrosiloxyl (-(Me)(H)Si—O—)$_x$—). In some embodiments, $R^{4a}$ can be triethylsilane, tetramethyldisiloxyl (—Si(Me)₂OSi(Me)₂H), pentamethyldisiloxyl (—Si(Me)₂OSi(Me)₃), or polymethylhydrosiloxyl (-(Me)(H)Si—O—)$_x$—). In some embodiments, $R^{4a}$ can be tetramethyldisiloxyl (—Si(Me)₂OSi(Me)₂H).

When $R^{4a}$ is a silyl group, the method of the present invention can include an acid treatment step to remove the silyl group. In some embodiments, wherein $R^{4a}$ is the silyl group, the method further comprises adding an acid to the reaction mixture, under conditions sufficient to prepare the compound of Formula I wherein $R^4$ is —OH. The acid can be any suitable acid useful for removing silyl groups. In some embodiments, the acid can be hydrochloric acid, sulfuric acid, phosphoric acid, or nitric acid. In some embodiments, the acid can be hydrochloric acid. The step of treating the compound of Formula I with acid can be performed under any suitable conditions to form the compound of Formula I wherein $R^4$ is —OH. For example, the conditions can include maintaining the reaction mixture at room temperature, or heating the reaction mixture at any suitable temperature up to 100° C. For example, the reaction mixture with acid can be heated at any temperature between about 25° C. and about 100° C., or between about 50° C. and 100° C., or between about 65° C. and 85° C. In some embodiments, the reaction mixture comprising acid is heated. In some embodiments, the reaction mixture comprising acid is heated at between about 65° C. and 85° C.

In some embodiments, the compound Formula I having the structure:

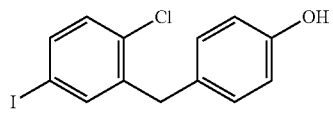 [SMILES: Oc1ccc(Cc2cc(I)ccc2Cl)cc1]

can be prepared by the method of the present invention, by forming the reaction mixture having the compound of Formula II with the structure:

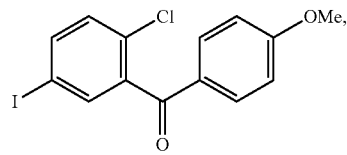 [SMILES: COc1ccc(C(=O)c2cc(I)ccc2Cl)cc1]

tetramethyldisiloxane (TMDS), a catalytic amount of B(C₆F₅)₃, and toluene, and adding hydrochloric acid to the reaction mixture, under conditions suitable to prepare the compound of Formula I.

IV. Compound of Formula III

The present invention also provides crystalline forms of, methods of crystallizing, and methods of preparing, the following compound:

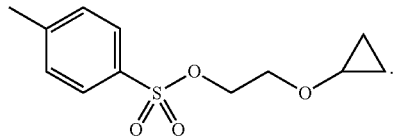 [SMILES: Cc1ccc(S(=O)(=O)OCCOC2CC2)cc1]

A. Crystalline Form of Formula III

In some embodiments, the present invention provides a crystalline form of the compound having the structure:

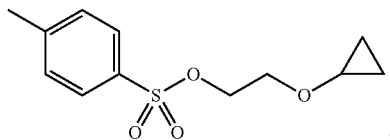

The crystalline compound of the present invention can be characterized by the X-ray powder diffraction (XRPD), the Raman spectra, the differential scanning calorimetry (DSC) endotherm, the thermal gravimetric analysis (TGA) showing decomposition temperature, and the unit cell of the crystal structure.

Figure 2:
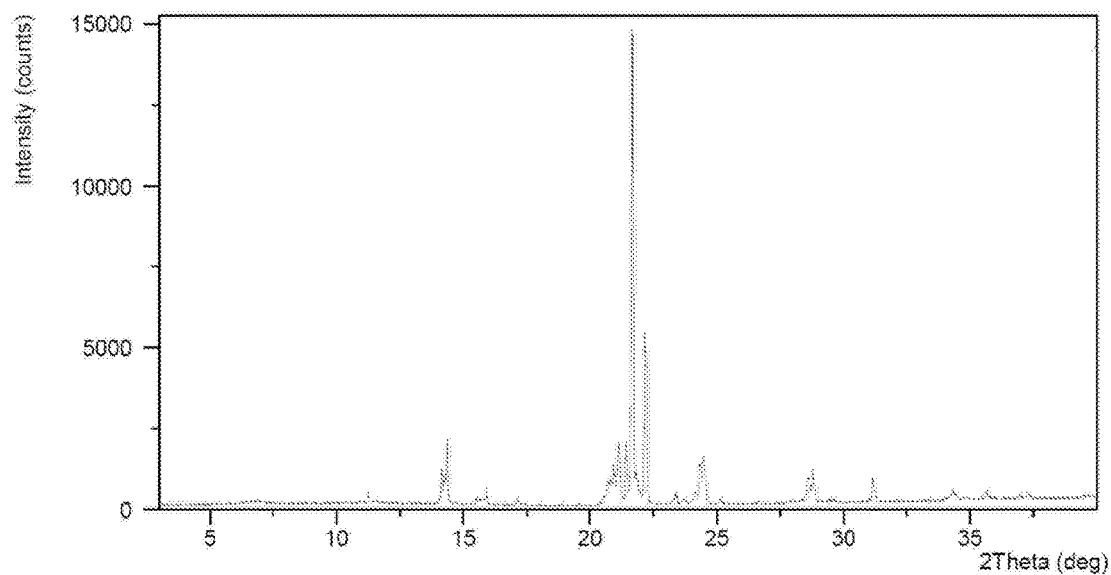
FIG. 2 provides the X-ray powder diffraction (XRPD) spectra of crystalline 2-cyclopropoxyethyl 4-methylbenzenesulfonate prepared from ethanol/water.
Figure 3:
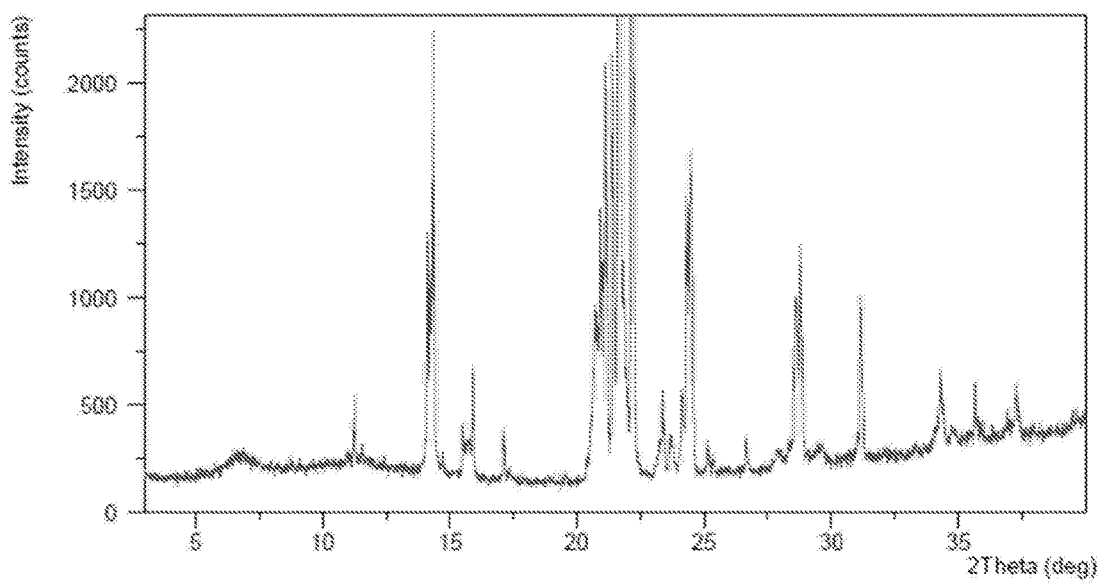
FIG. 3 shows an expanded version of the XRPD spectra in FIG. 2
Figures 5, 6:
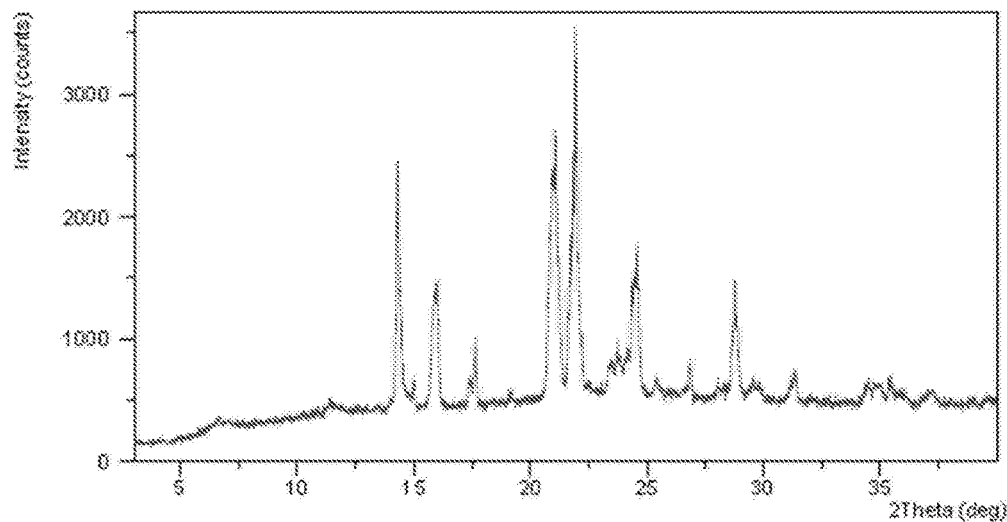
FIG. 5 provides the X-ray powder diffraction (XRPD) spectra of crystalline 2-cyclopropoxyethyl 4-methylbenzenesulfonate prepared from methanol/heptane.
FIG. 6 provides a Table of XRPD data for the XRPD spectra in FIG. 5.

In some embodiments, the present invention provides the crystalline form of the compound characterized by the XRPD substantially in accordance with that of FIG. 2 or FIG. 3 and the peaks substantially in accordance with the tables of FIG. 4. In some embodiments, the present invention provides the crystalline form of the compound characterized by the XRPD substantially in accordance with that of FIG. 5 and the peaks substantially in accordance with the tables of FIG. 6. The crystalline compound of the present invention can have any combination of peaks substantially in accordance with FIG. 4 or FIG. 6. Moreover, each peak listed in FIG. 4 and FIG. 6 can have an error range of ±0.2 degrees 2θ, preferably ±0.1 degrees 2θ.

In other embodiments, the crystalline form of the compound is characterized by an X-ray powder diffraction pattern that includes one or more peaks at 14.3, 15.8, 16.0, 17.6, 20.9, 21.1, 21.7, 21.8, 21.9, 24.3, 24.6, 26.8, and 28.8 degrees 2θ (±0.1 degrees 2θ), wherein said XRPD is made using CuK$_{α1}$ radiation. In another embodiment, the crystalline form of the compound is characterized by an XRPD that includes two or more, three or more, four or more, or five or more peaks at 14.3, 15.8, 16.0, 17.6, 20.9, 21.1, 21.7, 21.8, 21.9, 24.3, 24.6, 26.8, and 28.8 degrees 2θ (±0.1 degrees 2θ). In some embodiments, the crystalline form of the compound is characterized by an XRPD that includes peaks at 14.3, 21.1 and 21.9 degrees 2θ (±0.1 degrees 2θ). In some embodiments, the crystalline form of the compound is characterized by an XRPD that includes peaks at 14.3, 20.9, 21.1, 21.8, and 21.9 degrees 2θ (±0.1 degrees 2θ). In some embodiments, the crystalline form of the compound is characterized by an XRPD that includes peaks at 14.3, 16.0, 20.9, 21.1, 21.7, 21.8, 21.9, 24.3, 24.6 and 28.8 degrees 2θ (±0.1 degrees 2θ). In other embodiments, the crystalline form of the compound is characterized by the XRPD peaks substantially in accordance with FIG. 5.

Figure 7:
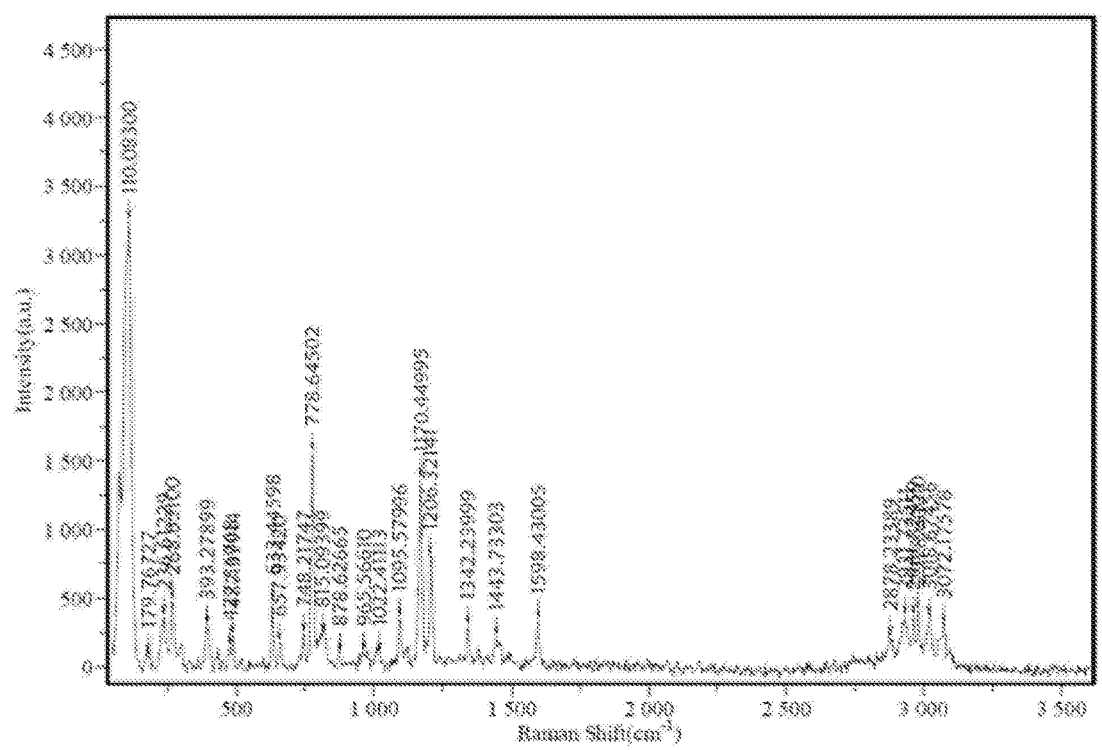
FIG. 7 provides the Raman spectra of crystalline 2-cyclopropoxyethyl 4-methylbenzenesulfonate prepared from methanol/heptane.
Figure 9:
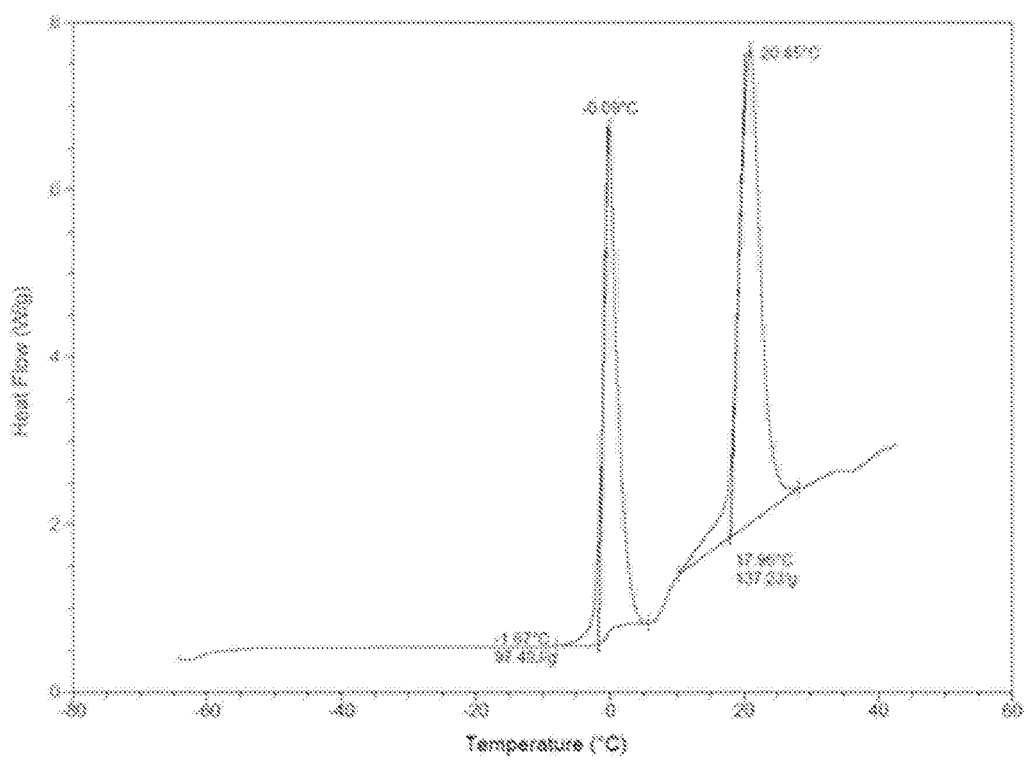
FIG. 9 provides a Differential Scanning calorimetry (DSC) chart of crystalline 2-cyclopropoxyethyl 4-methylbenzenesulfonate prepared from methanol/heptane. The peak at −0.09° C. is due to melting ice used to cool the sample.

The crystalline compound of the present invention is also characterized by the Raman spectra substantially in accordance with FIG. 7 and the peaks substantially in accordance with FIG. 8. In some embodiments, the crystalline form of the compound is characterized by a Raman spectra that includes one or more peaks at about 110, 236, 268, 393, 488, 633, 778, 1095, 1170, 1206, 1342, 1443, 1598, 2878, 2931, 3018, and 3072 cm$^{-1}$. In another embodiment, the crystalline form of the compound is characterized by a Raman spectra that includes two or more, three or more, four or more, or five or more peaks. In other embodiments, the crystalline form of the compound is characterized by the Raman spectra including peaks at about 110, 778, 1170, and 1206 cm$^{-1}$. In some other embodiments, the crystalline form of the compound is characterized by the Raman peaks substantially in accordance with FIG. 8.

The crystalline compound of the present invention is also characterized by the differential scanning calorimetry (DSC) endotherm. In some embodiments, the crystalline form of the compound is characterized by a DSC endotherm at about 21° C.

The crystalline compound of the present invention can also be characterized by unit cell data. Thermal gravimetric analysis (TGA) can also be used to characterize the crystalline compound of the present invention.

In some embodiments, the crystalline compound is characterized by at least one of the following: at least one XRPD peak as described above, at least one Raman peak as described above, and a DSC endotherm as described above. In other embodiments, the crystalline compound is characterized by at least two of the following: at least one XRPD peak as described above, at least one Raman peak as described above, and a DSC endotherm as described above. For example, the crystalline compound can be characterized by at least one XRPD peak and at least one Raman peak, or at least one XRPD peak and the DSC endotherm, or at least one Raman peak and the DSC endotherm, etc.

In some embodiments, the crystalline compound of the present invention is characterized by an X-ray powder diffraction (XRPD) pattern that includes one or more peaks at 14.3, 15.8, 16.0, 17.6, 20.9, 21.1, 21.7, 21.8, 21.9, 24.3, 24.6, 26.8, and 28.8 degrees 2θ (±0.1 degrees 2θ), wherein said XRPD is made using CuK$_{α1}$ radiation, and a Raman spectra that includes one or more peaks at about 110, 236, 268, 393, 488, 633, 778, 1095, 1170, 1206, 1342, 1443, 1598, 2878, 2931, 3018, and 3072 cm$^{-1}$. In other embodiments, the crystalline compound of the present invention is characterized by an X-ray powder diffraction (XRPD) pattern that includes one or more peaks at 14.3, 16.0, 20.9, 21.1, 21.7, 21.8, 21.9, 24.3, 24.6 and 28.8 degrees 2θ (±0.1 degrees 2θ), wherein said XRPD is made using CuK$_{α1}$ radiation, and a Raman spectra that includes one or more peaks at about 110, 778, 1170, and 1206 cm$^{-1}$.

In some embodiments, the crystalline form of the compound is characterized by an X-ray powder diffraction pattern that includes one or more peaks at 14.3, 21.4, 21.6, 21.7, 22.1, 22.2 and 24.4 degrees 2θ (±0.1 degrees 2θ), wherein said XRPD is made using CuK$_{α1}$ radiation. In another embodiment, the crystalline form of the compound is characterized by an XRPD that includes two or more, three or more, four or more, or five or more peaks at 14.3, 21.4, 21.6, 21.7, 22.1, 22.2 and 24.4 degrees 2θ (±0.1 degrees 2θ). In some embodiments, the crystalline form of the compound is characterized by an XRPD that includes peaks at 21.6, 21.7 and 22.1 degrees 2θ (±0.1 degrees 2θ). In some embodiments, the crystalline form of the compound is characterized by an XRPD that includes peaks at 14.3, 21.4, 21.6, 21.7, 22.1, 22.2 and 24.4 degrees 2θ (±0.1 degrees 2θ). In other embodiments, the crystalline form of the compound is characterized by the XRPD peaks substantially in accordance with FIG. 2 or FIG. 3.

In some embodiments, the present invention provides a crystalline form of a compound of the present invention which is isotopically labeled. Examples of isotopes that can be incorporated into compounds of the invention include, but are not limited to, isotopes of hydrogen, carbon, nitrogen, oxygen, fluorine, sulfur, and chlorine (such as $^2$H, $^3$H, $^{13}$C, $^{14}$C, $^{15}$N, $^{18}$O, $^{17}$O, $^{18}$F, $^{35}$S and $^{36}$Cl). Isotopically-labeled compounds and prodrugs thereof, as well as isotopically-labeled, pharmaceutically acceptable salts and prodrugs thereof, are within the scope of the present invention. Isotopically-labeled compounds of the present invention are useful in assays of the tissue distribution of the compounds and their prodrugs and metabolites; preferred isotopes for such assays include $^3$H and $^{14}$C. In addition, in certain circumstances substitution with heavier isotopes, such as deuterium ($^2$H), can provide increased metabolic stability, which offers therapeutic advantages such as increased in vivo half-life or reduced dosage requirements. Isotopically-labeled compounds of this invention and prodrugs thereof can generally be prepared according to the methods described herein by substituting an isotopically-labeled reagent for a non-isotopically labeled reagent.

B. Methods of Preparing Crystalline Forms of Formula III

In some embodiments, the present invention provides a method for preparing a crystalline form of a compound having the structure:

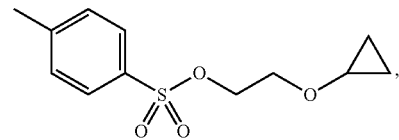 [SMILES: Cc1ccc(S(=O)(=O)OCCOC2CC2)cc1]

wherein the method includes a step (a) of mixing 2-cyclopropoxyethyl-4-methylbenzenesulfonate and a first solvent that is a polar protic solvent to form a solution, and a step (b) of adding a second solvent to the solution to provide a mixture, under conditions suitable to form the crystalline form of the compound.

The first solvent can be any suitable polar protic solvent. Polar protic solvents useful in the methods of the present invention include, but are not limited to, C$_{1-4}$ alcohols (methanol, ethanol, propanol, isopropanol, etc.), C$_{1-4}$ acids (formic acid, acetic acid, etc.) and water. In some embodiments, the polar protic solvent of step (a) can be a C$_{1-4}$ alcohol. For example, the polar protic solvent can be methanol, ethanol, propanol, isopropanol, butanol, isobutanol, sec-butanol, or tert-butanol. The polar protic solvent can be a single solvent or a mixture of solvents. In some embodiments, the polar protic solvent can be methanol or ethanol, or combinations thereof. In some embodiments, the polar protic solvent can be ethanol.

The second solvent can be any suitable solvent, such as a polar protic solvent or a non-polar solvent. Representative solvents include, but are not limited to, C$_{1-4}$ alcohols (methanol, ethanol, propanol, isopropanol, etc.), C$_{1-4}$ acids (formic acid, acetic acid, etc.), water, alkanes (pentanes, n-hexane, hexanes, n-heptane, heptanes, etc.), cycloalkanes (cyclopentane, cyclohexane, etc.), benzene, toluene, and 1,4-dioxane. In some embodiments, the second solvent can be a polar protic solvent or a non-polar solvent. The second solvent can be a single solvent or a mixture of solvents. In some embodiments, the second solvent can be water, pentanes, hexanes, petroleum ether, heptanes, cyclopentane or cyclohexane, or combinations thereof. In some embodiments, the second solvent can be water.

Any suitable combination of the first and second solvents can be used in the method of the present invention. In some embodiments, the first solvent can be ethanol and the second solvent can be water. In some embodiments, the first solvent can be methanol and the second solvent can be heptanes.

The first and second solvents can be present in any suitable ratio to one another. For example, the ratio of the first solvent to the second solvent can be about 10:1 (w/w), 5:1, 4:1, 3:1, 2.5:1, 2:1, 1.5:1, 1:1, 1:1.5, 1:2, 1:2.5, 1:3, 1:4, 1:5 or about 1:10 (w/w). In some embodiments, the ratio of the first solvent to the second solvent can be about 5:1 to about 1:1 (w/w). In some embodiments, the ratio of the first solvent to the second solvent can be about 2.5:1 (w/w).

The first solvent and the 2-cyclopropoxyethyl-4-methylbenzenesulfonate can be present in any suitable ratio. For example, the ratio of the first solvent to the 2-cyclopropoxyethyl-4-methylbenzenesulfonate can be about 10:1 (w/w), 5:1, 4:1, 3:1, 2.5:1, 2:1, 1.5:1, 1:1, 1:1.5, 1:2, 1:2.5, 1:3, 1:4, 1:5 or about 1:10 (w/w). In some embodiments, the ratio of the first solvent to the 2-cyclopropoxyethyl-4-methylbenzenesulfonate can be about 1:1 (w/w).

The method of crystallizing the compound of Formula III can include additional steps. For example, the method of crystallizing can include heating and cooling steps. The heating can assist in the dissolution of the 2-cyclopropoxyethyl-4-methylbenzenesulfonate, and the cooling can assist in the crystallization. The mixture can be heated to the boiling temperature of the solvent mixture. For example, the mixture can be heated to a temperature of less than about 30° C., 40, 50, 60, 70, 80, 90 or less than about 100° C. The heating can be for any suitable period of time, such as that necessary to dissolve the 2-cyclopropoxyethyl-4-methylbenzenesulfonate. For example, the heating can be for less than about 1 minute, or for 2, 3, 4, 5, 10, 15, 30, 60 minutes or longer. In some embodiments, the heating can be at a temperature of less than about 50° C. In some embodiments, the heating can be at a temperature of from about 20° C. to about 50° C.

When the mixture is cooled, the solvent mixture can be cooled quickly using an ice bath, or cooled slowly. The solvent mixture can also be cooled to room temperature, or to a temperature below room temperature. For example, the solvent mixture can be cooled to a temperature of less than about room temperature, or less than about 20° C., 15, 10, 5, or less than about 0° C. The solvent mixture can be maintained at the lower temperature for any suitable period of time, such as several hours, days or weeks. In some embodiments, the method of crystallizing also includes step (c) of heating the mixture at a temperature of from about 20° C. to about 50° C. until the mixture becomes clear; and step (d) of cooling the clear mixture to a temperature of less than about 10° C.

The solvent mixture can also contain a variety of other components, such as acids, bases and salts. Acids useful in the present invention include, but are not limited to, acetic acid, formic acid, hydrochloric acid, sulfuric acid, and other weak acids and strong acids. Bases useful in the present invention include, but are not limited to, ammonia, sodium hydroxide, and others. Salts useful in the present invention include, but are not limited to, sodium chloride, potassium chloride, potassium carbonate and others.

Crystallization can be induced by methods known in the art, for example by mechanical means such as scratching or rubbing the contact surface of the reaction vessel with e.g. a glass rod. Optionally the saturated or supersaturated solution may be inoculated with seed crystals. The method can also include use of a seed crystal of crystalline 2-cyclopropoxyethyl-4-methylbenzenesulfonate. In some embodiments, the mixture in the above methods includes a seed crystal of the crystalline compound of the present invention.

Isolation of the desired crystalline form can be accomplished by removing the solvent and precipitating solvent from the crystals. Generally this is carried out by known methods as for example filtration, suction filtration, decantation or centrifugation. Further isolation can be achieved by removing any excess of the solvent(s) from the crystalline form by methods known to the one skilled in the art as for example application of a vacuum, and/or by heating above −80° C., preferably in a temperature range below 80° C., even more preferably below 50° C.

The 2-cyclopropoxyethyl-4-methylbenzenesulfonate used in the crystallization method can be prepared using any suitable method. In some embodiments, the 2-cyclopropoxyethyl-4-methylbenzenesulfonate can be prepared by the method described below.

The crystallizing method of the present invention can provide the crystalline 2-cyclopropoxyethyl-4-methylbenzenesulfonate of the present invention and described above. In some embodiments, the product of step (b) can be the crystalline 2-cyclopropoxyethyl-4-methylbenzenesulfonate of the present invention.

C. Methods of Preparing Compound of Formula III

The present invention also provides methods of making the compound of Formula III. The compound of Formula III has been prepared previously (see U.S. Pat. No. 7,838,499). Following the Barbier-like magnesium mediated intramolecular ring opening/cyclization step described previously, the method of the present invention involves an extraction step using 2-methyl-tetrahydrofuran, where the extraction solvent, containing the intermediate compound 2-cyclopropoxyethanol, is used directly in the tosylation step without further concentration.

In some embodiments, the present invention provides a method of preparing a compound of Formula III:

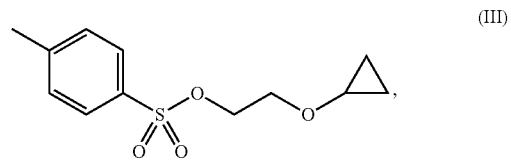 [SMILES: Cc1ccc(S(=O)(=O)OCCOC2CC2)cc1]
(III)

wherein the method includes a step (a) of forming a first reaction mixture including Mg and a compound having the structure:

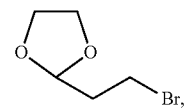

in tetrahydrofuran solvent, under conditions suitable to form an intermediate compound having the structure:

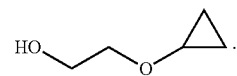

The method also includes a step (b) of contacting the first reaction mixture with water and 2-methyl-tetrahydrofuran such that the intermediate of step (a) is substantially dissolved in the 2-methyl-tetrahydrofuran. The method also includes a step (c) of forming a second reaction mixture with 4-methylbenzene-1-sulfonyl chloride (Tosyl-Cl) and the 2-methyl-tetrahydrofuran of step (b) containing the intermediate of step (a), under conditions suitable to form the compound of Formula III.

The method of preparing the compound of Formula III can include a number of other reagents. For example, the first reaction mixture in step (a) can include reagents such as, but not limited to, iodine ($I_2$) and 1,2-dibromoethane ($BrCH_2CH_2Br$). In some embodiments, the first reaction mixture also includes $BrCH_2CH_2Br$ and $I_2$. In some embodiments, the first reaction mixture includes $BrCH_2CH_2Br$, $I_2$, Mg and the compound having the structure:

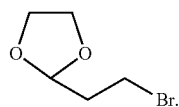

Following step (a), the first reaction mixture can be contacted with a variety of solvents, reagents and components in step (b). For example, the first reaction mixture can be contacted with water, acid, sodium chloride, among others, in step (b). The acid can be a mineral acid or an organic acid such as a carboxylic acid. Representative acids that can be used in step (b) include, but are not limited to, hydrochloric acid, formic acid, acetic acid, citric acid, lactic acid, oxalic acid, glycolic acid, and others. In some embodiments, the first reaction mixture can be contacted with water and an acid in step (b). In some embodiments, the acid can be hydrochloric acid, formic acid, acetic acid, citric acid, lactic acid, oxalic acid, or glycolic acid. In some embodiments, the acid can be hydrochloric acid. In some embodiments, the acid can be glycolic acid. In some embodiments, the first reaction mixture can be contacted with water and hydrochloric acid in step (b). In some embodiments, the first reaction mixture can be contacted with water and glycolic acid in step (b). In some embodiments, the first reaction mixture can also be contacted with sodium chloride in step (b).

The steps of the method can be performed under any suitable reaction conditions. For example, the temperature of each step can independently be from about −10 to about 100° C., or from about −10 to about 10° C., or from about 20 to about 60° C., or from about 30 to about 40° C. Alternatively, the temperature of each step can independently be about −10° C., 0, 10, 20, 30, 40, 50, 60, 70, 80, 90 or about 100° C. In some embodiments, the temperature of step (a) can be from about 20 to about 60° C. In some embodiments, the temperature of step (b) can be about room temperature. In some embodiments, the temperature of step (c) can be from about −10 to about 10° C.

The reaction time for each step of the method is suitable to substantially complete the application. For example, the time of each step can be several minutes to several hours. Each of steps (a) and (c) of the method can independently be from about 10 to about 30 hours.

The compound of Formula III can be prepared in any suitable yield using the method of the present invention. For example, the yield can be at least about 50% (mol/mol), 55, 60, 65, 70, 75, 80, 85, 90 or at least about 95% (mol/mol).

In some embodiments, the compound of Formula III can be prepared in at least 50% yield. In some embodiments, the compound of Formula III can be prepared in at least 65% yield.

The 2-methyl-tetrahydrofuran mixture of step (b) containing the intermediate of step (a), can be used in step (c) without forming a concentrated intermediate. In some embodiments, the 2-methyl-tetrahydrofuran containing the intermediate of step (a) is used in step (c) without removing the 2-methyl-tetrahydrofuran to form a concentrated intermediate.

The method of preparing the compound of Formula III can also be performed using the compound having the structure:

under similar conditions. Other conditions for preparing the compound of Formula III can be found in Tetrahedron Letters 1999, 40, 8647-8650.

D. Methods of Using Compound of Formula III

The present invention also provides methods of using the compound of Formula III for the preparation of other compounds. For example, the compound of Formula III has been used previously (see U.S. application Ser. No. 13/889, 980) to prepare compounds of Formula Ic:

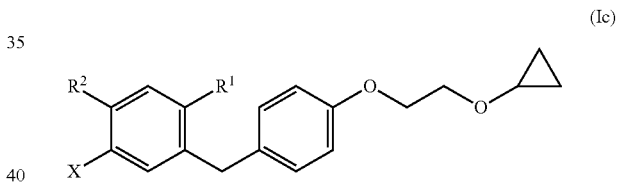

In some embodiments, the present invention provides a method of preparing the compound of Formula Ic:

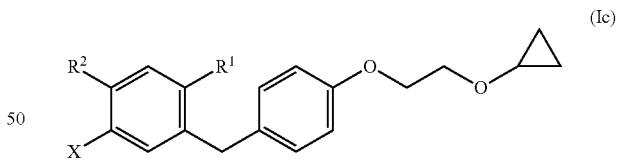

comprising forming a reaction mixture having a compound of Formula III having a purity of at least 90%, and a compound of Formula Ib:

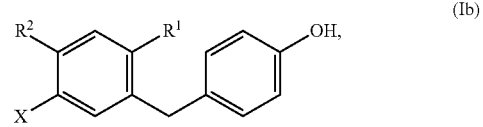

under conditions suitable to prepare the compound of Formula Ic, wherein X can be bromo or iodo. $R^1$ can be hydrogen, halo, hydroxy, $C_1$-$C_3$ alkyl or $C_1$-$C_3$ alkoxy. $R^2$ can be hydrogen, halo, hydroxy, $C_1$-$C_3$ alkyl, $C_1$-$C_3$ alkoxy, $C_3$-$C_6$ cycloalkyl, ($C_1$-$C_3$ alkoxy)$C_1$-$C_3$ alkyl, ($C_1$-$C_3$ haloalkoxy)$C_1$-$C_3$ alkyl, ($C_2$-$C_4$ alkenyloxy)$C_1$-$C_3$ alkyl, ($C_2$-$C_4$ alkynyloxy)$C_1$-$C_3$ alkyl, ($C_3$-$C_6$ cycloalkoxy)$C_1$-$C_3$ alkyl, $C_1$-$C_3$ hydroxyalkoxy, $C_3$-$C_6$ cycloalkoxy, $C_3$-$C_6$ heterocycloalkoxy, ($C_1$-$C_3$ alkoxy)$C_1$-$C_3$ alkoxy, ($C_1$-$C_3$ haloalkoxy)$C_1$-$C_3$ alkoxy, ($C_2$-$C_4$ alkenyloxy)$C_1$-$C_3$ alkoxy, ($C_2$-$C_4$ alkynyloxy)$C_1$-$C_3$ alkoxy, ($C_3$-$C_6$ cycloalkoxy)$C_1$-$C_3$ alkoxy, ($C_3$-$C_6$ heterocycloalkoxy)$C_1$-$C_3$ alkoxy, ($C_3$-$C_6$ cycloalkyl)$C_1$-$C_3$ alkoxy, ($C_3$-$C_6$ cycloalkyl)$C_2$-$C_4$ alkenyloxy or ($C_3$-$C_6$ cycloalkyl)$C_2$-$C_4$ alkynyloxy.

The compound of Formula III can have any suitable purity of at least 90%. For example, the compound of Formula III can have a purity of at least 90, 91, 92, 93, 94, 95, 96, 97, 98 or 99%. In some embodiments, the compound of Formula II can have a purity of at least 95%. In some embodiments, the compound of Formula II can have a purity of at least 97%.

In some embodiments, the compounds include those where $R^1$ can be halo. In other embodiments, $R^1$ can be F, Cl, Br or I. In some other embodiments, $R^1$ can be Cl.

In some embodiments, the compounds include those where $R^2$ can be H.

In some embodiments, the compound has the structure wherein $R^1$ can be halo; $R^2$ can be H. In other embodiments, the compound has the structure wherein $R^1$ can be chloro; $R^2$ can be H. In some embodiments, the compound has the structure where $R^1$ can be chloro; $R^2$ can be H; and X can be iodo.

The method of preparing the compound of Formula Ic can be performed under any suitable conditions. For example, the reaction mixture can include a base. The base can include inorganic bases such as, but not limited to, cesium carbonate, potassium carbonate, sodium carbonate, or mixtures thereof. In some embodiments, the base can include cesium carbonate. In some embodiments, the base can include potassium carbonate. In some embodiments, the base can include a mixture of cesium carbonate and potassium carbonate.

The method of preparing the compound of Formula Ic can also include an ammonium salt. Representative ammonium salts include, but are not limited to, tetramethylammonium bromide, tetramethylammonium iodide, tetramethylammonium hydroxide and tetrabutylammonium iodide. In some embodiments, the reaction mixture also includes tetrabutylammonium iodide.

The compound of Formula III can be in any suitable physical form for the method of making the compound Formula Ic. For example, the compound of Formula III can be an oil or a crystal as described above. In some embodiments, the compound of Formula III is crystalline. In some embodiments, the compound of Formula III is the crystalline form described above.

In some embodiments, the compound of Formula Ic has the structure:

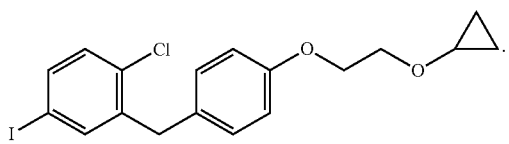 [SMILES: Clc1ccc(I)cc1Cc1ccc(OCCOC2CC2)cc1]

In some embodiments, the compound of Formula Ib has the structure:

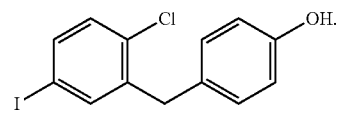

In some embodiments, the method of preparing the compound of Formula Ic includes forming the reaction mixture having $Cs_2CO_3$, $K_2CO_3$, tetrabutylammonium iodide, the crystalline compound of Formula III, and the compound of Formula Ib having the structure:

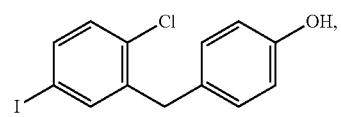

under conditions suitable to prepare the compound of Formula Ic having the structure:

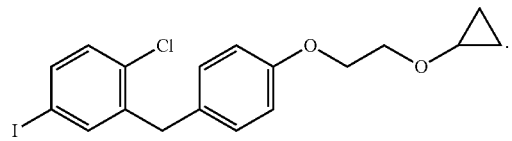 [SMILES: Clc1ccc(I)cc1Cc1ccc(OCCOC2CC2)cc1]

The compound of Formula Ib can be prepared by any means available in the art. In some embodiments, the compound of Formula Ib used in the method of making the compound of Formula Ic, can be prepared by the methods of the present invention described above.

The alkyl, alkoxy, cycloalkyl, alkenyloxy, alkynyloxy, cycloalkoxy, hydroxyalkoxy, and heterocycloalkoxy groups or portions of Formula Ic can optionally be partially or completely fluorinated. And one or more hydrogen atoms of Formula Ic can optionally be substituted with deuterium.

V. Examples

The following examples are offered for illustrative purposes, and are not intended to limit the invention in any manner. Those of skill in the art will readily recognize a variety of noncritical parameters which can be changed or modified to yield essentially the same results.

The names of compounds shown in the following examples were derived from the structures shown using the CambridgeSoft Struct=Name algorithm as implemented in ChemDraw Ultra version 10.0. Unless otherwise indicated, the structures of compounds synthesized in the examples below were confirmed using the following procedures:

(1) Gas chromatography-mass spectra with electrospray ionization (MS ESI) were obtained with an Agilent 5973N mass spectrometer equipped with an Agilent 6890 gas chromatograph with an HP-5 MS column (0.25 µm coating; 30 m×0.25 mm). The ion source was maintained at 230° C. and spectra were scanned from 25-500 amu at 3.09 sec per scan.

(2) High pressure liquid chromatography mass spectra (LC-MS) were obtained using Finnigan Surveyor HPLC equipped with a quaternary pump, a variable wavelength detector set at 254 nm, an XB-C18 column (4.6×50 mm, 5 µm), and a Finnigan LCQ ion trap mass spectrometer with electrospray ionization. Spectra were scanned from 80-2000 amu using a variable ion time according to the number of ions in the source. The eluents were B: acetonitrile and D: water. Gradient elution from 10% to 90% B in 8 min at a flow rate of 1.0 mL/min is used with a final hold at 90% B of 7 min. Total run time is 15 min.

(3) Routine one-dimensional NMR spectroscopy was performed on 400 MHz or 300 MHz Varian Mercury-Plus spectrometers. The samples were dissolved in deuterated solvents obtained from Qingdao Tenglong Weibo Technology Co., Ltd., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for $CD_3CN$, 3.30 ppm for $CD_3OD$, 5.32 ppm for $CD_2Cl_2$ and 7.26 ppm for $CDCl_3$ for $^1H$ spectra.

Example 1. Preparation of 4-(2-chloro-5-iodobenzyl)phenol (1)

A reduction-demethylation reaction has been developed. The method uses tetramethyldisiloxane as a reducing agent and tris(pentafluorophenyl)borane as a catalyst. After the siloxane hydrolysis, the crude 4-(2-chloro-5-iodobenzyl)phenol was easily purified by trituration in n-heptanes or petroleum ether (the 30 to 60° C. (mainly hexane isomers fraction) or 90 to 100° C. (mainly heptane isomers fraction)) which readily removes impurities and the ortho isomer. Both fractions removed the impurities well but the heptanes fraction is preferred for safety reasons.

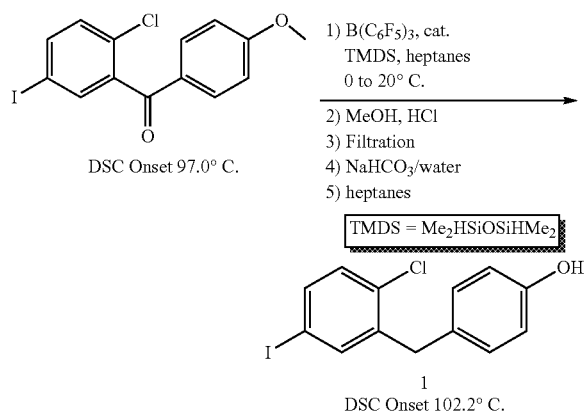

Solution 1:

A 1 L flask was charged with petroleum ether (0.2 L) and tris(pentafluorophenyl)borane (907 mg, 1.77 mmol) under nitrogen with stirring. The solution was cooled to 0 to 5° C., and tetramethyl-1,1,3,3-disiloxane (TMDS) (143 g, 1.06 mol) in an addition funnel was added dropwise over 15 min.

A 5 L four-necked glass flask was charged with (2-chloro-5-iodophenyl)(4-methoxyphenyl)methanone (220 g, 590.5 mmol) and petroleum ether (1.0 L). The mixture was cooled to 0 to 5° C., and the Solution 1 was added dropwise to it over 50 min while the reaction temperature was kept below 10° C. The mixture was stirred for 6 hours at 20° C. and monitored by TLC and/or LCMS. To the solution at 20° C. was carefully added hydrochloric acid in methanol (6 N, 720 mmol, 240 mL) and the mixture was stirred at 120 rpm for 6 hours.

Deionized water (1200 mL) was added and the mixture was stirred for 30 minutes. The mixture was filtered and the filter cake was washed with water (500 mL), 5% $NaHCO_3$ (500 mL), water (500 mL) and petroleum ether (2×250 mL). The filter cake was dried under reduced pressure (0.09 MPa) at 70° C. to give 4-(2-chloro-5-iodobenzyl)phenol as a white solid (236 g).

| COMPOUND | DESCRIPTION | LCMS RT (MIN) | HPLC RT (MIN) 50% TO 100% | % RANGE IN CRUDE |
|---|---|---|---|---|
| Product | | 3.9 | 13.8 | >98 |
| Impurity A | 4-((2-chloro-5-iodophenyl) (hydroxy)methyl)phenol | | | 0-1 |
| Impurity B | 2-(2-chloro-5-iodobenzyl)phenol | 4.0 | 14.9 | 0 to 0.3 |

Example 2. Large-Scale Preparation of 4-(2-chloro-5-iodobenzyl)phenol (1)

Solution 1:

A 2 L flask was charged with petroleum ether (1 L, 90 to 100° C. fraction) and tris(pentafluorophenyl)borane (3.44 g, 6.71 mmol) under nitrogen with stirring. The solution was cooled to 0 to 5° C., and TMDS (143 g, 2.42 mol) in an addition funnel was added dropwise over 15 min.

A 5 L four-necked glass flask was charged with (2-chloro-5-iodophenyl)(4-methoxyphenyl)methanone (500 g, 1.34 mol) and petroleum ether (2.0 L). The mixture was cooled to 0 to 5° C., and the Solution 1 was added dropwise to it over 1.5 h while keeping the reaction temperature below 20° C. as the gas evolved from the solution. The mixture was stirred for 16 hours at 20 to 30° C. and monitored by LCMS. To the solution at 20° C. was carefully added hydrochloric acid (357 g, 3.6 mol) in methanol (237 g) and the mixture was stirred at 120 rpm for 0.5 h at 20 to 30° C., and warmed to 75 to 85° C. for 16 h while a precipitate formed.

The mixture was filtered and the filter cake was washed with water (2×1 L), 5% $NaHCO_3$ (1 L) and petroleum ether (2×500 mL). The filter cake was dried under reduced pressure (0.09 MPa) at 55° C. for 16 h to give 4-(2-chloro-5-iodobenzyl)phenol as a white solid. Yield: 422 g (91.3%). $^1H$ NMR (400 MHz, $CDCl_3$) δ 7.46 (m, 2H), 7.07 (m, 3H), 6.78 (d, J=8.6 Hz, 2H), 4.73 (s, 1H), 3.96 (s, 2H). MS ESI (m/z) calculated: 344. found 343 $[M-H]^-$, 687 $[2M-H]^-$.

| COMPOUND | DESCRIPTION | LCMS RT (MIN) | HPLC RT (MIN) 50% TO 100% | % RANGE IN CRUDE |
|---|---|---|---|---|
| Product | | 3.9 | 13.8 | >98 |
| Impurity A | 4-((2-chloro-5-iodophenyl) (hydroxy)methyl)phenol | | | 0-1 |
| Impurity B | 2-(2-chloro-5-iodobenzyl)phenol | 4.0 | 14.9 | 0 to 0.3 |

Example 3. Large-Scale Preparation of 4-(2-chloro-5-iodobenzyl)phenol (1)

Solution 1:

In a glass lined reactor (2-chloro-5-iodophenyl)(4-methoxyphenyl)methanone (15.8 kg) and toluene (94.8 kg) were charged under nitrogen and the reaction mixture was concentrated to reflux in order to remove water and alcohol traces. After cooling to room temperature the weight of distillate was replaced by fresh anhydrous toluene. Tetramethyldisiloxane (5.7 kg) was then charged and the solution was transferred under nitrogen into plastic drum.

Solution 2:

In a glass lined reactor tris(pentafluorophenyl)borane (0.123 kg) and toluene (13.9 kg) were charged under nitrogen and the reaction mixture was stirred until dissolution and packed into plastic drum under inert atmosphere.

Solution 3:

In a glass lined reactor tetramethyldisiloxane (5.7 kg) and toluene (13.9 kg) were charged under nitrogen and the reaction mixture was cooled to −5 to 0° C. Solution 2 was added to Solution 3 over 1 hour maintaining the temperature below 5° C. At the end of addition the reaction mixture was stirred 15 minutes and Solution 1 was added to Solution 3 over 4 hours at a temperature between −3 to 15° C. The mixture was then stirred for 3 hours at 12-15° C.

The reaction mixture was then cooled to 0-10° C. and a solution of methanol (31.6 kg) and aqueous acid chloride (6.5 kg) was added and stirred for 12 h. Water (43 kg) was then added and the phases separated. Organic phase was washed with brine (48 kg) and concentrated under reduced pressure. Heptane B (44.2 kg) was then charged and the mixture was allowed to cool overnight. After 3 h stirring at 0-5° C. the cake was filtered and washed with cold heptane (7 kg). The product (13.5 kg/Yield: 92.4%) was obtained as white powder after drying. NMR and MS matched those shown in Example 2.

Example 4. Large-Scale Preparation of 4-(2-chloro-5-iodobenzyl)phenol (1)

Solution 1:

In a glass lined reactor (2-chloro-5-iodophenyl)(4-methoxyphenyl)methanone (200.0 kg/1.0 equiv) and toluene (1200 kg) were charged under nitrogen and the solution was distilled until 200 kg of solvents were removed from the reaction mixture in order to purge potential water and alcohol traces. After cooling to room temperature tetramethyldisiloxane (72 kg/1.0 eq.) was charged, and the solution was transferred and packed under nitrogen into plastic drums.

Solution 2:

In a glass lined reactor tris(pentafluorophenyl)borane (1.56 kg/0.006 equiv) and toluene (176 kg) were charged under nitrogen and the reaction mixture was stirred until dissolution and packed into plastic drum under inert atmosphere.

Solution 3:

In a glass lined reactor tetramethyldisiloxane (72 kg/1.0 eq.) and toluene (176 kg) were charged under nitrogen and the reaction mixture was cooled to −5° C. Solution 2 was added to Solution 3 over 30 minutes keeping the temperature below 5° C. At the end of addition the reaction mixture was stirred 15 minutes and Solution 1 was added to Solution 3 over 3.45 h at a temperature between −3 to 15° C. The mixture was then stirred for 3 h at 12-15° C.

The reaction mixture was then cooled to 0-10° C. and a solution of methanol (400 kg) and 33% hydrochloric acid (82 kg) was added. At the end of addition the reaction was heated at 15-20° C. and stirred for 8-12 h.

Water (544 kg) was added and layers were separated. Organic layer was washed with brine (150 kg NaCl in 461 kg of water). After filtration of organic layer, solvent was removed under reduced pressure without exceeding 60° C. Heptane B (560 kg) was then charged at 50-55° C. The reaction mixture was stirred 2 hours at 50-55° C. and allowed to cool at 0-5° C. After 3 h stirring at 0-5° C. the cake was filtered and washed with precooled 0-5° C. heptane B (100 kg). Wet product (200 kg) was then dried under vacuum at 40° C. during 24 hours. After drying 148.9 kg of the title compound (yield=80.5%) was obtained as a white powder. NMR and MS matched those shown in Example 2.

Example 5a. Preparation of 2-cyclopropoxyethyl 4-methylbenzenesulfonate (2)

The title compound was prepared in two steps from 2-(2-bromoethyl)-1,3-dioxolane using a Barbier-like magnesium mediated intramolecular ring opening/cyclization.

Preparation of 2-cyclopropoxyethanol

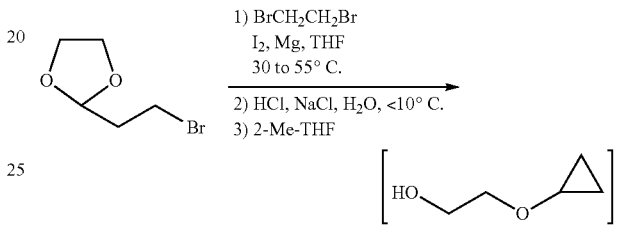

A 1500 L glass-lined reactor equipped with bottom fed nitrogen sparging was charged with THF (200 kg, 1.67 eq) with stirring (80 RPM) followed by the addition of magnesium turnings (27.4 kg, 1.7 eq) and iodine (1.0 kg, 0.06 eq). The mixture was warmed to between 30 to 40° C. and a nitrogen-sparged solution of 1,2-dibromoethane (5.0 kg) in THF (20.0 kg) was added dropwise. Once the Grignard reaction commenced, a solution of 1,2-dibromoethane (53.6 kg) in THF (250.0 kg) was added over 10 h while keeping the internal temperature about 50° C.

After the addition was complete, the solution of 2-(2-bromoethyl)-1,3-dioxolane (120.0 kg, 1.0 eq) in THF (270.0 kg, 2.25 w/w) was added slowly over 10 h, while keeping the internal temperature about 50° C. The reaction mixture was stirred at 40-50° C. for 20 h while copious amounts of white solids (probably magnesium (II) bromide) formed.

Under nitrogen sparging, the mixture was cooled to 0° C. and de-oxygenated water (160 kg) was added very slowly while keeping the internal temperature below 10° C. Concentrated hydrogen chloride (67.2 kg, 0.56 eq) was added to a saturated solution of brine (420 kg) with efficient stirring. This resulting HCl-brine solution was added very slowly to the Grignard reaction mixture while keeping the temperature below 10° C. The mixture was stirred at 10 to 20° C. for 2 h before the organic layer was separated and the aqueous layer was extracted with 2-methyltetrahydrofuran (3×160 kg).

Preparation of 2-cyclopropoxyethyl 4-methylbenzenesulfonate (2)

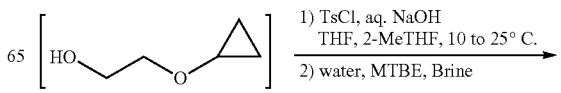

-continued

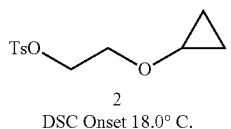

2
DSC Onset 18.0° C.

The above organic solution of 2-cyclopropoxyethanol was cooled to 0° C. and an aqueous solution of sodium hydroxide (80.0 kg) in water (300.0 kg) was added. p-Toluenesulfonyl chloride (151.0 kg, 1.2 eq) was added over 8 h while keeping the internal temperature below 5° C. The reaction mixture was cooled to 0° C. and stirred for another 16 h. Cooling was stopped and the phases were separated while the mixture slowly warmed to 20 to 25° C. The aqueous layer was diluted with water (240.0 kg) and extracted with MTBE (180.0 kg). The combined organic phases were washed with saturated brine (240.0 kg). The organic layer was concentrated under reduced pressure (while keeping the bath temperature below 45° C.) to give an oil (130 kg).

Absolute ethanol (156.0 kg) was added to the above oil. De-ionized water (65.0 kg) was added and the mixture was gently warmed to about 30° C. until the solution became clear. The solution was cooled to 0° C. and stirred for 5 h at −5 to 0° C. The solids were filtered. The solids (120.0 kg) were added to absolute ethanol (135.0 kg). De-ionized water (57.5 kg) was added and the mixture gently warmed until the solution became clear (about 30° C.). The mixture was cooled to 0° C., and then cooled for 5 h at −5 to 0° C. The mixture was filtered and the solids collected and dried under vacuum to give 107 kg of the title compound (66.3% yield). $^1$H NMR (400 MHz, CDCl3) δ 7.82 (d, J=8.4 Hz, 2H), 7.36 (d, J=8.4 Hz, 2H), 4.17 (t, J=4.8 Hz, 2H), 3.70 (t, J=4.8 Hz, 2H), 3.30-3.24 (m, 1H), 2.47 (s, 3H), 0.55-0.42 (m, 4H). DSC onset 18° C.

Alternatively, a 40 mL of glass bottle was charged with the above oil (1.0 g) and methanol/n-hexane (10:1, 5 mL) with stirring at 30 to 35° C. After the mixture became a clear solution, the mixture was cooled to −10 to −5° C. and stirred for another 4 hours. The mixture was filtered and the filter cake was dried under freeze drying for over 24 hours to give a white solid. Yield: 0.82 g (82.0%).

Example 5b. Crystallization of 2-cyclopropoxyethyl 4-methylbenzenesulfonate (2)

Crystallization conditions for compound 2 are found in the following tables:

|  | Quant. (g) | Cryst. Solvents V/W = 2 | Cryst. Temp. (° C.) | Cryst. Time (h) | Yield (%) | Compound 2 15.2 min | Side Product A 16.9 min | Side Product B 13.3 min | Side Product C 15.0 min |
|---|---|---|---|---|---|---|---|---|---|
| Crude | 27.4 |  |  |  | 64 | 97.6 | 0.37 | 0.3 | 0.3 |
| Cryst. | 20 | 3:1 EtOH/H$_2$O | −10 to −2 | 3 | 73 | 99.6 | 0.18 | 0.05 | 0.06 |
| Recryst. |  | 3:4 EtOH/n-Hex. | 0 to 5 | 3 | 73 | 99.9 | 0.08 | 0.01 | 0.01 |

|  | Quant. (g) | Seed Cryst. | Cryst. Solvents V/W = 2 | Cryst. Temp. (° C.) | Cryst. Time (h) | Yield (%) | Compound 2 15.2 min | Side Product A 16.9 min | Side Product B 13.3 min | Side Product C 15.0 min |
|---|---|---|---|---|---|---|---|---|---|---|
| Crude | 96.5 |  |  |  |  | 68 | 95.1 | 0.29 | 2 | 0.42 |
| Cryst. | 76.7 | Yes | 6:2:3$^a$ EtOH/H$_2$O/n-Hex. | −10 to −2 | 3 | 79 | 98.8 | 0.22 | 0.61 | 0.11 |
| 1$^{st}$ | 70.0 | Yes | 3:4 EtOH/n-Hex. | −10 to −4 | 3 | 91 | 99.5 | 0.18 | 0.22 | 0.03 |
| 2$^{nd}$ | 63.4 | Yes | 3:4 EtOH/n-Hex. | −2 to 3 | 4.5 | 90 | 99.8 | 0.14 | 0.06 | 0 |
| 3$^{rd}$ | 56.4 | No | 1:1 EtOH/n-Hex. | −3 to 2 | 3 | 89 | 99.9 | 0.07 | 0.04 | 0 |

$^a$V/W = 2.25

| Treatment Method |  | Quant. (g) | Yield (%) | Seed Cryst. | Cryst. Solvents V/W = 2 | Cryst. Temp. | Cryst. Time (h) | Cpd 2 15.2 min | Side Product A 16.9 min | Side Product B 13.3 min | Side Product C 15.0 min | Side Product D 17.6 min |
|---|---|---|---|---|---|---|---|---|---|---|---|---|
| Without wash | Crude | 37.7 | 91 |  |  |  |  | 94.8 | 0.32 | 0.74 | 0.50 | 0.90 |
|  | Cryst. | 25.4 | 67 | Yes | 3:2:1 EtOH/n-hex./H2O |  | 4 | 99.3 | 0.02 | 0.36 | 0.02 | 0.06 |
|  | Recrys. | 23.5 | 92 | No | 1:1 EtOH/n-Hex. |  | 4 | 99.6 | 0.01 | 0.30 | 0.01 | 0.06 |
| Wash 1X with 15% brine | Crude | 33.2 | 80 |  |  |  |  | 95.5 | 0.12 | 0.56 | 0.50 | 0.78 |
|  | Cryst. | 22.9 | 69 | Yes | 1:1 EtOH/n-Hex. | −10 to −4 | 4 | 99.3 | 0.10 | 0.10 | 0.07 | 0.27 |
|  | Recrys. | 19.4 | 85 | No | 1:1 EtOH/n-Hex. | −10 to 3 | 4 | 99.8 | 0.03 | 0.07 | 0.01 | 0.08 |
| Wash 1X with 15% brine containing 0.1M CuSO$_4$ | Crude | 33.8 | 82 |  |  |  |  | 95.5 | 0.18 | 0.57 | 0.49 | 0.66 |
|  | Cryst. | 26.5 | 78 | Yes | 2:1 EtOH/H2O | −10 to 0 | 3 | 99.3 | 0.02 | 0.28 | 0.04 | 0.12 |

Side Products A and B have the following structures:

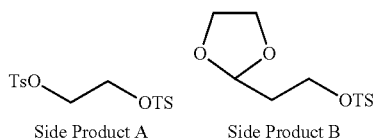

Side Product A    Side Product B

Other solvents used: 3:1 EtOH:water, 2:1 EtOH:water, 3:4 EtOH:n-hexane, 6:2:3 EtOH:water:n-hexane, 3:2:1 EtOH:water:n-hexane, 1:1 EtOH:n-hexane, 3:4 EtOH:n-heptane and 1:1 MeOH:n-heptane.

Example 6. Preparation of 2-cyclopropoxyethyl 4-methylbenzenesulfonate (2)

The title compound was prepared in two steps from 2-(2-bromoethyl)-1,3-dioxolane using a Barbier-like magnesium mediated intramolecular ring opening/cyclization.

Preparation of 2-cyclopropoxyethanol

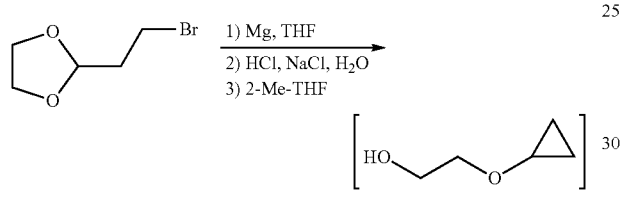

A round-bottom flask equipped with a thermometer, magnetic stirrer, condenser and addition funnel was purged with nitrogen and was charged with anhydrous THF (44 mL) and magnesium (4.5 g, 0.185 mole). After stirring and sparging with nitrogen at ambient temperature (23 to 28° C.), 2-(2-bromoethyl)-1,3-dioxolane (3 g, 2.0 mL, 15 mmol) was added in one portion. After stirring, the reaction was initiated (a water bath was used to maintain the outer temperature below 30° C.).

The remaining 2-(2-bromoethyl)-1,3-dioxolane (27 g, 17.7 mL, 0.15 mole) in THF (30 ml) was added to the mixture via a suitable addition funnel under nitrogen sparging at a rate that kept the internal temperature at 45° C. to 60° C. (the outer temperature of water bath was kept 20° C. to 30° C.). After the addition was warmed to 60° C. and stirred under nitrogen sparging overnight.

A nitrogen-sparged aqueous solution of 37% hydrochloric acid (16.4 g) and sodium chloride (18.2 g) in water (93 g) was added dropwise to the reaction mixture while keeping the internal temperature between −15° C. and −10° C. The reaction mixture was warmed to 10° C. to 15° C. The reaction was extracted with three 35 ml portions of 2-methyltetrahydrofuran. The combined organic solution was directly used for the next step.

Preparation of 2-cyclopropoxyethyl 4-methylbenzenesulfonate (2)

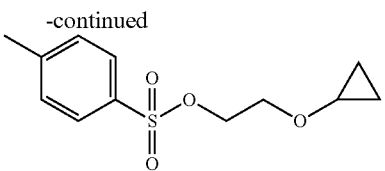

A round-bottom flask equipped with a thermometer, mechanical stirrer, condenser and addition funnel was purged with nitrogen and was charged with the above solution of 2-cyclopropoxyethanol in 2-methyltetrahydrofuran. The mixture was cooled to −5° C. to 0° C. with stirring. An aqueous solution of NaOH (20.1 g) in water (87 mL) was added dropwise to the mixture while keeping the internal temperature between −5° C. and 0° C. 4-Methylbenzenesulfonyl chloride (37.8 g) was added while keeping the internal temperature between 0° C. and 5° C. The reaction was stirred at 0° C. to 5° C. under nitrogen for another 5 hours in a cooling bath. The cooling bath was removed and the reaction was warmed slowly to 10° C. to 20° C. and stirred overnight.

Brine (57 g water and 15 g NaCl) was added to the reaction. The mixture was extracted with ethyl acetate/petroleum ether (38 ml EtOAc and 8 ml PE, three times). The combined organic layers were washed with saturated brine (54 g) and water (30 mL), and then concentrated under reduced pressure at 35-40° C. to give the crude product as a liquid. Yield: 32 g (75%).

Example 7. Preparation of 2-cyclopropoxyethyl 4-methylbenzenesulfonate (2)

The title compound was prepared in two steps from 2-(2-bromoethyl)-1,3-dioxolane using a Barbier-like magnesium mediated intramolecular ring opening/cyclization.

Preparation of 2-cyclopropoxyethanol

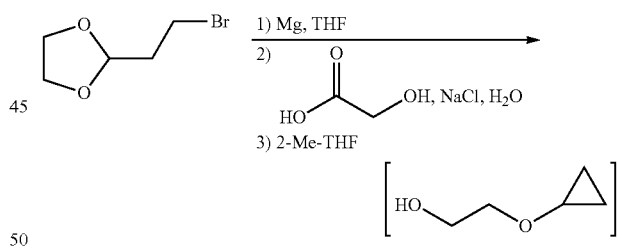

A four-necked 2 L flask equipped with a thermometer, magnetic stirrer, condenser and addition funnel was purged with nitrogen and was charged with anhydrous THF (500 mL) and magnesium (30 g, 1.2 mole). After stirring and sparging with nitrogen for 45 minutes at ambient temperature (23 to 28° C.), 2-(2-bromoethyl)-1,3-dioxolane (20 g, 13.1 mL, 0.1 mole) was added in one portion. After stirring for 5 minutes, the reaction was initiated and the internal temperature rose from 25° C. to 45° C. (a water bath was used to maintain the outer temperature below 30° C.).

The remaining 2-(2-bromoethyl)-1,3-dioxolane (180 g, 118.1 mL, 1.0 mole) was added to the mixture via a suitable addition funnel over 2.5 hours under nitrogen sparging at a rate that kept the internal temperature at 40° C. to 60° C. (the outer temperature of water bath was kept 20° C. to 30° C.). After the addition was completed, the reaction was cooled slowly to 20° C. to 30° C. over 4 hours. The reaction was then warmed to 60° C. and stirred under nitrogen sparging overnight.

Nitrogen-sparged water (200 g, 11.1 mole) was added dropwise to the reaction mixture over 1 hour while keeping the temperature between −15° C. and −10° C. (deionized water was degassed by sparging with nitrogen for 40 minutes before addition). A nitrogen-sparged aqueous solution of glycolic acid (75.6 g, 0.99 mole) and sodium chloride (100 g, 1.7 mol) in water (400 g, 22.2 mole) was added dropwise to the reaction mixture over 3 hours while keeping the internal temperature between −15° C. and −10° C. (the aqueous solution was degassed by sparging with nitrogen for 1 hour before addition). After the addition was completed, the reaction was stirred at −15 to −10° C. for 10 minutes. The reaction mixture was warmed to 10° C. to 15° C. The reaction was extracted with three 200 g portions of 2-methyltetrahydrofuran. The combined organic solution was directly used for the next step.

Preparation of 2-cyclopropoxyethyl 4-methylbenzenesulfonate (2)

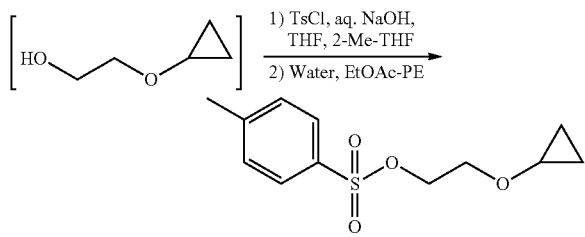

A four-necked 3 L flask equipped with a thermometer, mechanical stirrer, condenser and addition funnel was purged with nitrogen and was charged with the above solution of 2-cyclopropoxyethanol in THF and 2-methyltetrahydrofuran. The mixture was cooled to −5° C. to 0° C. with stirring (100 rpm). A precooled (0° C.) aqueous solution of NaOH (134 g, 3.3 mole) in water (580 mL) was added dropwise to the mixture over 40 minutes while keeping the internal temperature between −5° C. and 0° C. The mixture was stirred for another 20 minutes at −5° C. to 0° C. 4-Methyl-benzenesulfonyl chloride (252 g, 1.32 mole) was added portion-wise over 40 minutes while keeping the internal temperature between −5° C. and 0° C. The reaction was stirred at −5° C. to 0° C. under nitrogen for another 5 hours in a cooling bath. The cooling bath was removed and the reaction was warmed slowly to 10° C. to 20° C. and stirred overnight.

Brine (400 mL) was added to the reaction. The mixture was extracted with ethyl acetate/petroleum ether (fractions: 60° C. to 90° C.) (5:1 v/v, 300 mL×3). The combined organic layers were washed with saturated brine (300 mL) and water (200 mL), and then concentrated under reduced pressure at 40° C. to give the crude product as a liquid (215.6 g, yield: 76%, purity: 99.0%). To the crude product was added 200 g of ethanol and evaporated under reduced pressure (~0.1 MPa) at 40° C. to remove any residual solvents.

Example 8. Preparation of 2-(4-(2-Cyclopropoxyethoxy)Benzyl)-1-Chloro-4-Iodobenzene This example describes the preparation of 2-(4-(2-cyclopropoxyethoxy)benzyl)-1-chloro-4-iodobenzene via coupling of the 4-(2-chloro-5-iodobenzyl)phenol with 2-cyclopropoxyethyl 4-methylbenzenesulfonate.

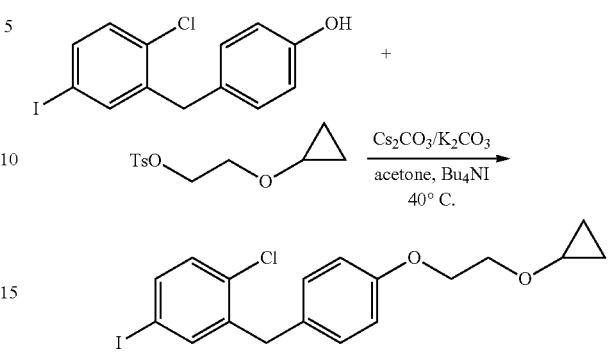

Under nitrogen a 500 L glass-lined reactor was charged with acetone (123 kg) with stirring (120 RPM), 4-(2-chloro-5-iodobenzyl)phenol (19.37 kg, 0.056 kmol), 2-cyclopropoxyethyl 4-methylbenzenesulfonate (15.85 kg, 0.062 kmol), cesium carbonate (18.31 kg, 0.0562 kmol) powder, potassium carbonate (23.3 kg, 0.169 kmol) powder and TBAI (4.15 kg, 0.011 kmol). After stirring for 40-45 h at 40° C., TLC (petroleum ether (30-60° C. fraction):ethyl acetate=4:1, Rf=0.3) showed that starting material was consumed. The mixture was cooled to 20-25° C.

The reaction mixture was filtered over diatomite (28 kg) and the filter cake was washed with acetone (2×31 kg). The combined filtrates were transferred to a 500 L glass-lined reactor and concentrated. The residue was dissolved in ethyl acetate (175 kg, washed with water (2×97 kg) and concentrated until the volume was about 100 L and was transferred to a 200 L glass-lined reactor and continued to concentrate to get about 22.5 kg of crude material.

The crude material was dissolved in methanol/n-hexane (10:1, 110 kg) under refluxing for 30 min with stirring (100 RPM) until it was a clear solution. The mixture was cooled to 5 to 10° C. and some crystal seeds (20 g) were added. The suspension was stirred for another 5 h at 5 to 10° C. The mixture was filtered at 0 to 5° C. and the filter cake was washed with pre-cooled methanol/n-hexane (10:1, 5° C., 2×11 kg). The filter cake was dried under reduced pressure (0.09 MPa) at 15 to 20° C. for 15 h to give off-white to white solid. Yield: 18.1 kg, 75%. Melting Point: 31° C. (DSC onset). $^1$H NMR (CDCl$_3$, 400 MHz): δ 7.45-7.50 (m, 2H), 7.09-7.12 (m, 3H), 6.88 (d, J=8.8 Hz, 2H), 4.11 (t, J=5.2 Hz, 2H), 3.99 (s, 2H), 3.88 (t, J=5.2 Hz, 2H), 3.40-3.44 (m, 1H), 0.63-0.67 (m, 2H), 0.49-0.54 (m, 1H). MS ESI (m/z): 429 [M+1]$^+$. $^{13}$C NMR (CDCl$_3$, 100 MHz): δ 157.5, 141.5, 139.5, 136.6, 134.2, 131.2, 130.8, 129.9, 114.9, 91.66, 69.00, 67.13, 53.72, 38.08, 5.63.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing a compound of Formula III:

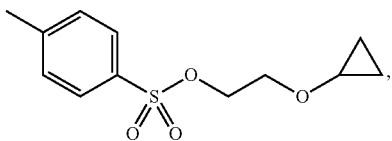

the method comprising:
(a) forming a first reaction mixture comprising Mg and a compound having the structure:

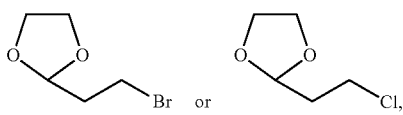

in tetrahydrofuran solvent, under conditions suitable to form an intermediate compound having the structure:

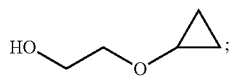

(b) contacting the first reaction mixture with water and 2-methyl-tetrahydrofuran such that the intermediate of step (a) is substantially dissolved in the 2-methyl-tetrahydrofuran; and
(c) forming a second reaction mixture comprising 4-methylbenzene-1-sulfonyl chloride (Tosyl-Cl) and the 2-methyl-tetrahydrofuran of step (b) containing the intermediate of step (a), under conditions suitable to form the compound of Formula III,
wherein the 2-methyl-tetrahydrofuran containing the intermediate of step (a) is used in step (c) without removing the 2-methyl-tetrahydrofuran to form a concentrated intermediate.

2. The method of claim 1, wherein the compound of step (a) is

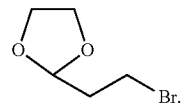

3. The method of claim 1, wherein the first reaction mixture in step (a) further comprises $I_2$.

4. The method of claim 1, wherein the first reaction mixture in step (a) further comprises $BrCH_2CH_2Br$.

5. The method of claim 1, wherein the first reaction mixture in step (a) further comprises $BrCH_2CH_2Br$ and $I_2$.

6. The method of claim 1, wherein step (b) comprises contacting the first reaction mixture with water, an acid, and 2-methyl-tetrahydrofuran such that the intermediate of step (a) is substantially dissolved in the 2-methyl-tetrahydrofuran.

7. The method of claim 6, wherein step (b) comprises contacting the first reaction mixture with water, an acid, sodium chloride and 2-methyl-tetrahydrofuran such that the intermediate of step (a) is substantially dissolved in the 2-methyl-tetrahydrofuran.

8. The method of claim 7, wherein the acid is selected from the group consisting of hydrochloric acid, formic acid, acetic acid, citric acid, lactic acid, oxalic acid, and glycolic acid.

9. The method of claim 8, wherein the acid is hydrochloric acid.

10. The method of claim 8, wherein the acid is glycolic acid.

11. The method of claim 1, wherein the second reaction mixture of step (c) further comprises tetrahydrofuran (THF).

12. The method of claim 1, wherein the compound of Formula III is prepared in at least 50% yield.

13. The method of claim 12, wherein the compound of Formula III is prepared in at least 65% yield.

14. The method of 1, wherein at least about 75% of the intermediate of step (a) is dissolved in the 2-methyl-tetrahydrofuran in step (b).

15. The method of 1, wherein at least about 90% of the intermediate of step (a) is dissolved in the 2-methyl-tetrahydrofuran in step (b).

* * * * *